US008877718B2

(12) United States Patent
Bringmann et al.

(10) Patent No.: US 8,877,718 B2
(45) Date of Patent: Nov. 4, 2014

(54) ANTIINFECTIVE AND ANTITUMORAL COMPOUNDS ISOLATED FROM TROPICAL LIANAS

(75) Inventors: Gerhard Bringmann, Wuerzburg (DE); Stefan Rüdenauer, Worms (DE); Reto Brun, Therwil (CH); Andreas Irmer, Fuellinsdorf (CH); Ralf Bargou, Höchberg (DE); Manik Chatterjee, Wuerzburg (DE); Anastasia Voskobojnik, Oehringen (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 720 days.

(21) Appl. No.: 12/865,333

(22) PCT Filed: Feb. 6, 2009

(86) PCT No.: PCT/EP2009/000855
§ 371 (c)(1),
(2), (4) Date: Nov. 22, 2010

(87) PCT Pub. No.: WO2009/098082
PCT Pub. Date: Aug. 13, 2009

(65) Prior Publication Data
US 2011/0059911 A1   Mar. 10, 2011

(30) Foreign Application Priority Data

Feb. 6, 2008 (DE) .......................... 10 2008 007 898
May 16, 2008 (EP) ..................................... 08009112

(51) Int. Cl.
C07C 46/00 (2006.01)
C07C 50/32 (2006.01)
C07C 49/513 (2006.01)
C07C 49/517 (2006.01)
C07D 317/70 (2006.01)
C07H 15/20 (2006.01)
A61K 31/122 (2006.01)
A61K 31/704 (2006.01)
A61P 35/00 (2006.01)
A61P 31/00 (2006.01)

(52) U.S. Cl.
CPC .................. *C07C 50/32* (2013.01); *C07C 46/00* (2013.01); *C07D 317/70* (2013.01); *C07H 15/20* (2013.01)
USPC ............ 514/25; 514/463; 514/682; 536/18.1; 549/433; 568/328

(58) Field of Classification Search
CPC ...... C07C 46/00; C07C 50/32; C07D 317/70; C07H 15/20
USPC ............ 514/25, 463, 682; 536/18.1; 549/433; 568/328
See application file for complete search history.

(56) References Cited

U.S. PATENT DOCUMENTS 4,252,951 A * 2/1981 Jackson et al. ................. 540/220
5,561,164 A * 10/1996 Gutteridge et al. ........... 514/682

FOREIGN PATENT DOCUMENTS

WO  WO 00/08495      * 2/2000 ............... G02B 5/00
WO  WO 2007/125196 A1 * 11/2007 ............ C07C 271/22

OTHER PUBLICATIONS

Trisha Gura, Science, Nov. 1997, pp. 1041-1042.*
Braga, Chem. Comm. 2005, 29, 3635-3645.*
The Merck manual 1992, pp. 4-5 and 24-25.*
Nicolaou et al, J. Am. Chem. Soc., 2004, 126, 607-12.*
Chai et al, Tetrahedron Letters, 2001, 42, 8915-17.*
Govidachari et al, Indian Journal of Chemistry, 1971, 9(10), 1042-43.*
Bringmann et al., "Antitumoral and antileishmanial dioncoquinones and ancistroquinones from cell cultures of *Triphyophyllum peltatum* (Dioncophyllaceae) and *Ancistrocladus abbreviatus* (Ancistrocladaceae)," *Phytochemistry*, 2008, pp. 2501-2509, vol. 69, No. 13.
Brockmann et al., "Rubromycins, III. The constitution of α-rubromycin, β-rubromycin, γ-rubromycin, and γ-*iso*-rubromycin," *Chemische Berichte*, 1970, pp. 1709-1726, vol. 103, No. 6.
Chai et al., "Concise formal total synthesis of hybocarpone and related naturally occurring naphthazarins," *The Journal of Organic Chemistry*, 2006, pp. 992-1001, vol. 71, No. 3.
Database: Beilstein [Online], XP002526698, Database Accession No. 2588151, corresponding to Berg et al., *Journal of Antibiotics*, 2000, pp. 1293-1295, vol. 53, No. 11.
Database: Beilstein [Online], XP002526699, Database Accession No. 3961775, corresponding to Govindachari et al., *Indian Journal of Chemistry*, 1971, pp. 1042, vol. 9.
Database: Beilstein [Online], XP002526700, Database Accession No. 2297104, corresponding to Anderson et al., *Journal of Chemical Society*, 1965, pp. 2141-2144.
Database: Beilstein [Online], XP002526701, Database Accession No. 5639361, corresponding to Cannon et al., *Australian Journal of Chemistry*, 1980, pp. 1073-1093, vol. 33, No. 5.
Database: Beilstein [Online], XP002526702, Database Accession No. 5793172, corresponding to Daliacker et al., *Zeitschrift Fuer Naturforschung, Teil B: Anorganische Chemie, Organische Chemie*, 1986, pp. 1273-1280, vol. 41, No. 10.

(Continued)

*Primary Examiner* — Ganapathy Krishnan
(74) *Attorney, Agent, or Firm* — Saliwanchik, Lloyd & Eisenschenk

(57) ABSTRACT

The present invention relates to naphthoquinone derivatives isolated from solid callus cultures from two species of the palaeotropical plant families Dioncophyllaceae and Ancistrocladaceae. It further relates to methods of their production as well as to their use as antiinfective and antitumoral pharmaceuticals.

9 Claims, 13 Drawing Sheets

(56) References Cited

OTHER PUBLICATIONS

Database: Beilstein [Online], XP002526703, Database Accession No. 5619417, corresponding to Rizzacasa et al., *Journal of the Chemistry Society, Perkin Transactions 1: Organic and Bio-Organic Chemistry*, 1987, pp. 2017-2022.

Glazunov et al., "Chemistry of naphthazarin derivatives: 8. Determination of structures of substituted 2-hydroxy-6(7)-methoxynaphthazarins and 7(8)-hydroxypyranonaphthazarins by IR spectroscopy," *Russian Chemical Bulletin*, Jan. 2001, pp. 95-100, vol. 50, No. 1, XP002526696.

Glazunov et al., "Chemistry of naphthazarin derivatives: 9. Direct observation (poly)hydroxynaphthazarins by IR spectroscopy," *Russian Chemical Bulletin*, Jan. 2003, pp. 198-207, vol. 52, XP002526697.

Nicolaou et al., "Total synthesis of hybocarpone and analogues thereof. A facile dimerization of naphthazarins to pentacyclic systems," *Journal of the American Chemical Society*, 2004, pp. 607-612, vol. 126, No. 2.

Veshkurova et al., "Malvone A, a phytoalexin found in *Malva sylvestris* (family Malvaceae)," *Phytochemistry*, 2006, pp. 2376-2379, vol. 67, No. 21.

\* cited by examiner

A

B

A

1b

B

A

B

A

1d

B

1d

A

B

A

B

C

D

E

F

G

H

I

ANTIINFECTIVE AND ANTITUMORAL COMPOUNDS ISOLATED FROM TROPICAL LIANAS

CROSS REFERENCE TO A RELATED APPLICATION

This application is a National Stage Application of International Application Number PCT/EP2009/000855, filed Feb. 6, 2009; which claims priority to German Application No. 102008007898.0, filed Feb. 6, 2008 and European Patent Application. No. 08009112.7, filed May 16, 2008; all of which are incorporated herein by reference in their entirety.

The present invention relates to naphthoquinone derivatives isolated from solid callus cultures from two species of the palaeotropical plant families Dioncophyllaceae and Ancistrocladaceae. It further relates to methods of their production as well as to their use as antiinfective and antitumoral pharmaceuticals.

According to the WHO 2004 world health report, infectious diseases are still the number one cause of death. Particularly in developing countries millions of people die each year from diseases like malaria, African sleeping sickness, Chagas disease, or leishmaniasis, which are all caused by protozoans. In parts the medicaments presently employed are often only insufficiently effective, difficult to obtain in many places, and have many side effects. In addition to these disadvantages, the increasing development of resistances against established agents demands the search for novel, highly active and specific lead structures.

Multiple myeloma is a malignant hematological tumor, which is characterized by the clonal proliferation of terminally differentiated B cells, the antibody-producing plasma cells, in the bone marrow. Monoclonal antibodies excessively secreted by the malignant plasma cell clone are mostly detectable in the peripheral blood. According to a study from the American Cancer Society, multiple myeloma was the second most frequent hematological form of tumor in 2007 (P. J. Hayden, C. S. Mitsiades, K. C. Anderson, P. G. Richardson, Curr. Opin. Hematol. 2007, 14, 609-615). Despite an extension of the average life expectancy of the patients of 1-2 years to about 5 years, in particular by the introduction of high-dose chemotherapy with melphalan followed by autologous stem cell transplantation and the introduction of novel agents, such as lenalidomid and bortezomib, the disease can only be temporarily repressed and remains incurable to a large extent. Thus, there is an urgent need for novel medicamentous options.

Non-Hodgkin lymphomas (NHL) are the most frequent hematological neoplasias. With a percentage of more than 80% of the aggressive B-NHLs, the diffuse large cell lymphomas represent the largest entity of the B-NHLs. It is assumed that the cell of origin of the diffuse large cell B-NHL is a germinal center B cell which, due to uninhibited cell division and concomitant absence of programmed cell death, leads to enhanced growth and expansion of a malignant B cell clone. With the introduction of the monoclonal anti-CD20 antibody (rituximab) as a therapeutic tool, a standard therapy using the combination of cytostatic chemotherapy (cyclophosphamid, doxorubicin, vincristin, and prednisone) and the monoclonal anti-CD20 antibody has been established within the last decade, which results in a permanent cure for about 40% of the patients. However, particularly patients having a bad prognostic risk profile often suffer from a disease relapse, whose chemotherapeutic treatment is much more difficult. Therefore, novel medicamentous options, in particular for this group of patients, are needed (A. Molina, Annu. Rev. Med. 2008, 59, 237-250).

For hundreds of years, plants have been an important source of pharmacologically active substances, and the search for novel natural products from the extracts of various parts of plants is still an important pillar of modern drug research. The phytochemical analysis of tropical lianas of the families Dioncophyilaceae and Ancistrocladaceae led to the discovery of a plurality of novel natural products exhibiting a broad spectrum of antiinfective activities (G. François, G. Bringmann, J. D. Phillipson, L. Aké Assi, C. Dochez, M. Rübenacker, C. Schneider, M. Wery, D. C. Warhust, G. C. Kirby, Phytochemistry 1994, 35, 1461-1464; M. R. Boyd, Y. F. Hallock, J. H. Cardellina II, K. P. Manfredi, J. W. Blunt, J. B. McMahon, R. W. Buckheit Jr., G. Bringmann, M. Schaefer, J. Med. Chem. 1994, 37, 1740-1745; G. Bringmann, V. Hoerr, U. Holzgrabe, A. Stich, Pharmazie 2003, 58, 343-346; A. Ponte-Sucre, J. H. Faber, T. Gulder, I. Kajahn, S. E. H. Pedersen, M. Schultheis, G. Bringmann, H. Moll, Antimicrob. Agents Chemother. 2007, 51, 188-194). The cultivation of these tropical lianas under modified conditions as well as the establishment of callus cultures from sterile plant parts expose the plants to chemical and physical stress (G. Bringmann, D. Feineis, J. Exp. Botany 2001, 52, 2015-2022) and thereby cause the formation of secondary metabolites. For example, the two 1,4-naphthoquinones plumbagin and droserone were detected in callus cultures of Triphyophyllum peltatum (Hutch. & Dalz.) Airy Shaw (Dioncophyllaceae) and Ancistrocladus abbreviatus Airy Shaw (Ancistrocladaceae) (G. Bringmann, M. Wohlfarth, H. Rischer, J. Schlauer, Tetrahedron Lett. 1998, 39, 8445-8448; G. Bringmann, H. Rischer, M. Wohlfarth, J. Schlauer, L. Aké Assi, Phytochemistry 2000, 53, 339-343). Given the known antitumoral activities of such naphthoquinones (P. U. Devi, F. E. Solomon, A. C. Sharada, Pharm. Biol. 1999, 37, 231-236; G. J. Kapadia, V. Balasubramanian, H. Tokuda, T. Konoshima, M. Takasaki, J. Koyama, K. Tagahaya, H. Nishino, Cancer Lett. 1997, 113, 47-53; A. Morello, M. Pavani, J. A. Garbarino, M. C. Chamy, C. Frey, J. Mancilla, A. Guerrero, Y. Repetto, J. Ferreira, Comp. Biochem. Physiol. 1995, 112C, 119-128), it seems highly rewarding to induce the formation of novel bioactive compounds with improved activities and selectivities by modifying the cultivation conditions of cell cultures of suitable plants.

Accordingly, it was an object of the present invention to provide further bioactive substances, suitable for the treatment of infectious diseases and tumors, in particular for the therapy of multiple myeloma and B cell lymphoma, as well as methods for their production.

The objects of the present invention are solved by a compound having the general formula

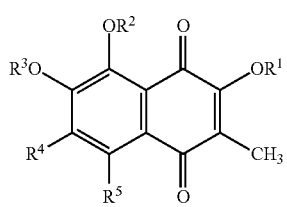

1 wherein $R^1$, $R^2$, and $R^3$ are independently selected from the group comprising (a) H, (b) an unsubstituted, monosubstituted, or polysubstituted $C_1$-$C_{18}$ alkyl, wherein said alkyl is straight, branched or cyclic, (c) a monosubstituted or polysubstituted $C_1$-$C_{18}$ alkenyl, wherein said alkenyl is straight, branched or cyclic, (d) an unsubstituted, monosubstituted, or polysubstituted aryl or heteroaryl, (e) an unsubstituted, monosubstituted, or polysubstituted benzyl group, (f) an acyl group, such as formyl, acetyl, trichloroacetyl, fumaryl, maleyl, succinyl, benzoyl, or acyl groups being branched, heteroatom-substituted or aryl-substituted, (g) a sugar or another acetal, and (h) a sulfonyl group, such as —$SO_2CH_3$, —$SO_2CF_3$, —$SO_2C_6H_4CH_3$ or $SO_2C_6H_4CH_2Br$;

$R^4$ and $R^5$ are independently selected from the group comprising (a') H, (b') an unsubstituted, monosubstituted, or polysubstituted $C_1$-$C_{18}$ alkyl, wherein said alkyl is straight, branched or cyclic, (c') a monosubstituted or polysubstituted $C_1$-$C_{18}$ alkenyl, wherein said alkenyl is straight, branched or cyclic, (d') an unsubstituted, monosubstituted, or polysubstituted aryl or heteroaryl, (e') an unsubstituted, monosubstituted, or polysubstituted benzyl group, (f') an acyl group, such as formyl, acetyl, trichloroacetyl, fumaryl, maleyl, succinyl, benzoyl, or acyl groups being branched, heteroatom-substituted or aryl-substituted, (g') a C- or O-linked sugar or another acetal, (h') —OH or —SH, (i') an alkoxy group, such as —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, wherein the alkyl group of said alkoxy group is straight, branched or cyclic, (j') an alkyl group bound via a sulfur atom, such as —$SCH_3$, —$SCH_2CH_3$, (k') a sulfonyl group, such as —$SO_3H$, —$SO_2CH_3$, —$SO_2CF_3$, —$SO_2C_6H_4CH_3$ or $SO_2C_6H_4CH_2Br$, (l') a nitrogen group, such as —$NH_2$, —NHR, —NRR' (with R, R' being an alkyl, aryl, heteroaryl, benzyl, alkenyl, alkinyl, acyl, or sulfonyl group), —NC or —$NO_2$, (m') —Fl, —Cl, —Br, —I, —CN, and (n') a hetero substituent; and $R^3$ and $R^4$ as well as $R^4$ and $R^5$ are optionally linked, thereby resulting in an unsubstituted, monosubstituted, or polysubstituted ring;

as well as salts and solvates thereof.

Particularly preferred are embodiments wherein (a) $R^1$ and $R^2$ are independently selected from the group comprising H and an unsubstituted, monosubstituted, or polysubstituted $C_1$-$C_{18}$ alkyl, wherein said alkyl is straight, branched or cyclic, (b) $R^3$ is selected from the group comprising H, an unsubstituted, monosubstituted, or polysubstituted $C_1$-$C_{18}$ alkyl, wherein said alkyl is straight, branched or cyclic, and a sugar or another acetal, which links $R^3$ and $R^4$ to form a five-membered ring, (c) $R^4$ is selected from the group comprising H and an alkoxy or an acetal, which links $R^3$ and $R^4$ to form a five-membered ring, and (d) $R^5$ and $R^6$ are independently selected from the group comprising H, hydroxy and an alkoxy group.

In a preferred embodiment said compound has the general formula

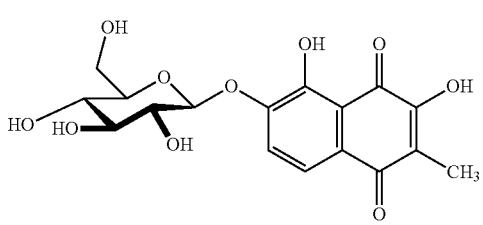

1a as well as derivatives, their diastereomers and respective enantiomers,
and salts and solvates thereof.

In another preferred embodiment said compound has the general formula

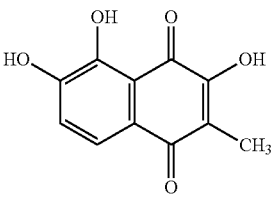

1b as well as derivatives,
and salts and solvates thereof.

In one preferred embodiment of the present invention said compound has the general formula

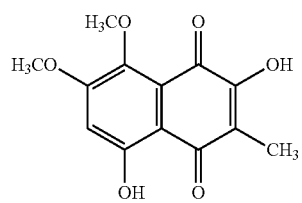

1c as well as derivatives,
and salts and solvates thereof.

In yet another embodiment said compound has the general formula

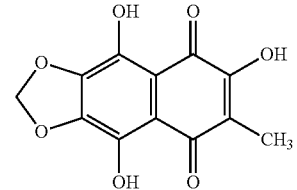

1d as well as derivatives,
and salts and solvates thereof.

In a preferred embodiment said compound has the general formula

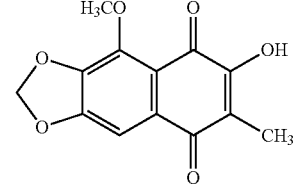

1e as well as derivatives,
and salts and solvates thereof.

Preferably, said salts and solvates are pharmaceutically acceptable salts and solvates.

The objects of the present invention are also solved by a compound, as defined above, for use as a pharmaceutical.

The objects are also solved by a compound, as defined above, for use in the treatment and/or prevention of diseases.

The objects are also solved by a compound, as defined above, for use in the treatment and/or prevention of tumoral and/or infectious diseases.

In one embodiment said infectious disease is Leishmaniasis.

In one embodiment said tumoral disease is multiple myeloma or B-cell lymphoma.

In one embodiment said compound is provided in form of a depot substance or as precursor, together with suitable pharmaceutically acceptable diluents or carrier substances.

In one embodiment said compound is provided in form of tablets, dragees, capsules, drop solutions, suppositories, preparations for injection or infusion for peroral, rectal, or parenteral administration. Such dosage forms as well as their manufacture are known to a person skilled in the art.

In one embodiment said compound is used in a concentration range between and including 5 µM and 500 µM, preferably 5 µM and 250 µM, more preferably 10 µM and 100 µM.

The objects of the present invention are also solved by the use of a compound, as defined above, as a tool for the examination and study of the mechanism of action of the antitumoral effects and as lead structure for the development of further antitumoral and antiinfective substances. The development of such substances can for example be based on further chemical derivatization of the compounds according to the present invention.

The objects of the present invention are also solved by a composition comprising a therapeutically effective amount of at least one compound, as defined above, together with suitable additives or excipients.

In one embodiment said composition is provided in form of a depot substance or as precursor, together with suitable pharmaceutically acceptable diluents or carrier substances.

In one embodiment said composition comprises at least one additional chemotherapeutic agent. Such chemotherapeutic agents can comprise any chemotherapeutic agent known to a person skilled in the art and commonly used in the course of a cancer therapy, such as mephalan, doxorubicin, and others. Ultimately, the choice of the chemotherapeutic agent is dependent on the kind of cancer and the individual needs of the patient.

In one embodiment said composition is provided in form of tablets, dragees, capsules, drop solutions, suppositories, preparations for injection or infusion for peroral, rectal, or parenteral administration. Such dosage forms as well as their manufacture are known to a person skilled in the art.

In one embodiment said composition comprises said compound in a concentration range between and including 5 µM and 500 µM, preferably 5 µM and 250 µM, more preferably 10 µM and 100 µM.

The objects of the present invention are also solved by a composition, as defined above, for use as a pharmaceutical.

The objects of the present invention are also solved by a composition, as defined above, for use in the treatment and/or prevention of diseases.

The objects of the present invention are also solved by a composition, as defined above, for use in the treatment and/or prevention of tumoral and/or infectious diseases.

The objects of the present invention are also solved by the use of a compound or a composition, as defined above, in the manufacture of a medicament for the treatment and/or prevention of diseases.

The objects are also solved by the use of a compound or a composition, as defined above, in the manufacture of a medicament for the treatment and/or prevention of tumoral and/or infectious diseases.

In one embodiment said infectious disease is Leishmaniasis.

In one embodiment said tumoral disease is multiple myeloma or B-cell lymphoma.

The objects of the present invention are further solved by a method of preparing a compound, as defined above, said method comprising the cultivation of callus cultures of tropical lianas of the families Dioncophyllaceae and Ancistrocladaceae as well as other related families under specifically optimized conditions and isolation of at least one compound, as defined above.

In one embodiment said method further comprises the synthetic derivatization of the isolated compound(s).

In a preferred embodiment said specific optimization of the cultivation conditions comprises the reduction of the main nutrition elements in the culture medium and the concomitant increase of the concentration of divalent ions in comparison to the other main nutrition elements. The main nutrition elements as well as their normal/standard (i.e. non-reduced) concentration can be derived from the composition of standard culture media, such as MS medium and LS medium.

In one embodiment the concentration of said main nutrition elements is reduced to ⅕ (20%) of the normal/standard concentration and the concentration of said divalent ions is reduced to ¼ (25%) of the normal/standard concentration.

In one embodiment said divalent ions are calcium and magnesium.

In one embodiment said isolation of at least one compound, as defined above, comprises extraction using an organic solvent or solvent mixture and preparative HPLC:

Cultivation conditions for existing callus cultures, preferably of *Triphyophyllum peltatum* (Hutch. & Dalz.) Airy Shaw and of *Ancistrocladus abbreviatus* Airy Shaw, were specifically optimized in order to obtain new metabolites. Compounds 1a-1e according to the present invention are released into the culture medium, but mostly accumulate in the biomass (plant cells).

*Triphyophyllum peltatum* (Hutch. & Dalz.) Airy Shaw and of *Ancistrocladus abbreviatus* Airy Shaw are members of the closely related palaeotropical plant families Dioncophyllaceae and Ancistrocladaceae from West Africa, which are in part characterized by a remarkable biochemical potential. However, other families of tropical plants are suitable as well.

In one embodiment of the present invention said other related families comprise other naphthoquinone-producing plants, such as Drosophyllaceae, Droseraceae, Nepenthaceae, Plumbaginaceae, Malvaceae, and Ebenaceae. Hereby, the compounds are either isolated directly from the plants or from their respective cell cultures.

In one embodiment of the present invention, the compound having the general formula 1 is produced by chemical synthesis or by biotechnological means, preferably by chemical synthesis.

For details of the chemical synthesis of the compound having the general formula 1 see Examples 2 and 4, in particular FIGS. 6 and 10.

In a preferred embodiment Dioncoquinone B (1b) is synthesized starting from or via the natural compound Ancistroquinone C (1f) (for details see Example 4B).

The objects of the present invention are also solved by a method of treatment of tumoral and/or infectious diseases, said method comprising the administration of a therapeutically effective amount of at least one compound, as defined above, to a patient.

In one embodiment said compound is administered in a concentration range between and including 5 µM and 500 µM, preferably 5 µM and 250 µM, more preferably 10 µM and 100 µM.

The term "substituent" as used herein is meant to refer to an atom or group of atoms substituted in place of a hydrogen atom on the parent chain of a hydrocarbon. Thus, the terms "unsubstituted", "monosubstituted", and "polysubstituted" refer to organic compounds wherein no hydrogen atom, one hydrogen atom, and at least two hydrogen atoms, respectively, are exchanged for another atom or group of atoms.

The term "derivative" as used herein is meant to refer to any compound derivable (e.g. by substitution of groups $R^1$ to $R^5$) from the compound having the general formula 1, as well as to mixtures of these various compounds. Notably, such mixtures may allow the preparation of "personalized" medicaments based on the kind of disease and the aetiopathology of the individual patient. Furthermore, the term "derivative" also refers to compounds having the general formula 1 and being isolated from other organisms than the exemplary tropical lianas, such as plants of other families, micro organisms, and animals.

The term "solvate" as used herein is meant to refer to crystalline solvates or solvent adducts, i.e. to compounds formed by solids (such as the compounds according to the present invention) and solvents. Solvates having water as solvent are referred to as hydrates. The ability of a solid (e.g. compound) to crystallize with a solvent is also called pseudo polymorphy.

The term "pharmaceutical" (or "medicament") as used herein is meant to refer to substances or preparations from substances destined for use on or in the human or animal body in order to cure, to alleviate, to prevent, or to diagnose diseases, ailments, medical/pathological conditions, or physical injuries.

The term "precursor" as used herein is meant to refer to a substance, which, after being administered to the human body, undergoes a transformation (e.g. due to the pH value inside the stomach) that results in one of the active compounds according to the present invention or its derivatives. The term also refers to derivatives of the compounds 1a-1e isolated from an organism, which serve as starting compounds for the synthesis of the respective compound 1a-1e in that particular organism and already have properties of the compounds according to the present invention.

The term "EC50" refers to the effective concentration to produce a 50% response (the term "ED50" refers to the effective dose to produce a 50% response).

The term "Dioncoquinone A" refers to a compound having the general formula 1a and the IUPAC name 3,5,6-trihydroxy-2-methyl-1,4-naphthoquinone-6-O-β-glucoside.

The term "Dioncoquinone B" refers to a compound having the general formula 1b and the IUPAC name 3,5,6-trihydroxy-2-methyl-1,4-naphthoquinone.

The term "Ancistroquinone D" refers to a compound having the general formula 1c and the IUPAC name 3,8-dihydroxy-5,6-dimethoxy-2-methyl-1,4-naphthoquinone.

The term "Ancistroquinone E" refers to a compound having the general formula 1d and the IUPAC name 3,5,8-trihydroxy-2-methyl-6,7-methylenedioxy-1,4-naphthoquinone.

The term "Ancistroquinone F" refers to a compound having the general formula 1e and the IUPAC name 3-hydroxy-5-methoxy-2-methyl-6,7-methylenedioxy-1,4-naphthoquinone.

The inventors have identified so far unknown natural compounds that can be isolated from specifically optimized cell cultures of two species of the palaeotropical plant families Dioncophyllaceae and Ancistrocladaceae.

Unexpectedly, the compounds having the general formula 1 possess very useful pharmacological characteristics. For example, Dioncoquinone A (3,5,6-trihydroxy-2-methyl-1,4-naphthoquinone-6-O-β-glucoside, 1a) and Dioncoquinone B (3,5,6-trihydroxy-2-methyl-1,4-naphthoquinone, 1b) have very distinct and unforeseen antiinfective, in particular antileishmanial, as well as antitumoral properties. Furthermore, these substances are non-toxic for normal, non-malignant blood cells, which makes them excellent candidates for the use in the treatment of various tumors or infective diseases.

As can be seen in the Examples section, these findings are based on solid experimentation: for example, the antitumoral effect was tested on two B cell lymphoma cell lines as well as two multiple myeloma cell lines, wherein normal peripheral mononuclear blood cells served as control cells.

Thanks to the extensive structural analysis of the various compounds, as disclosed herein, the compounds according to the present invention can now also be chemically synthesized in the laboratory as well as modified in order to obtain their derivatives and precursors. Strikingly, the inventors have also provided general methods for the chemical synthesis of compounds having the general formula 1.

Reference is now made to the figures, wherein

Figure 1:
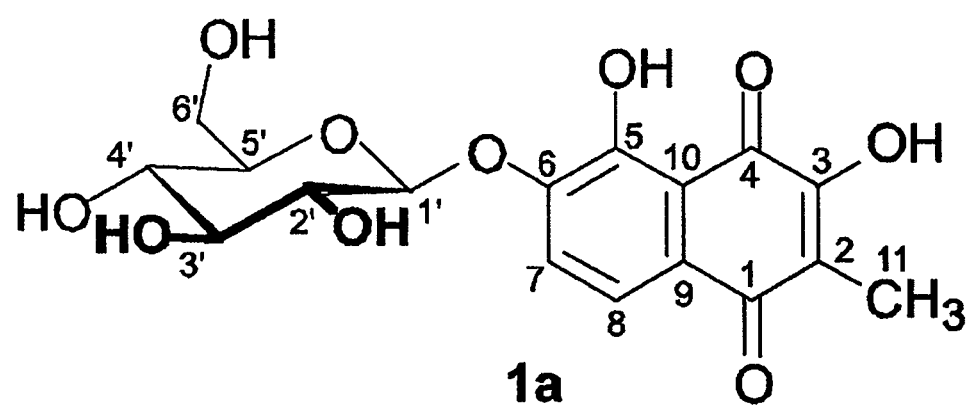
FIG. 1 shows Dioncoquinone A (1a) with C-atoms numbered 1-11 and 1'-6', respectively (A) as well as HMBC (single arrows) and $^1H,^1H$—COSY (double arrows) interactions relevant for the structural elucidation (B)
Figure 1:
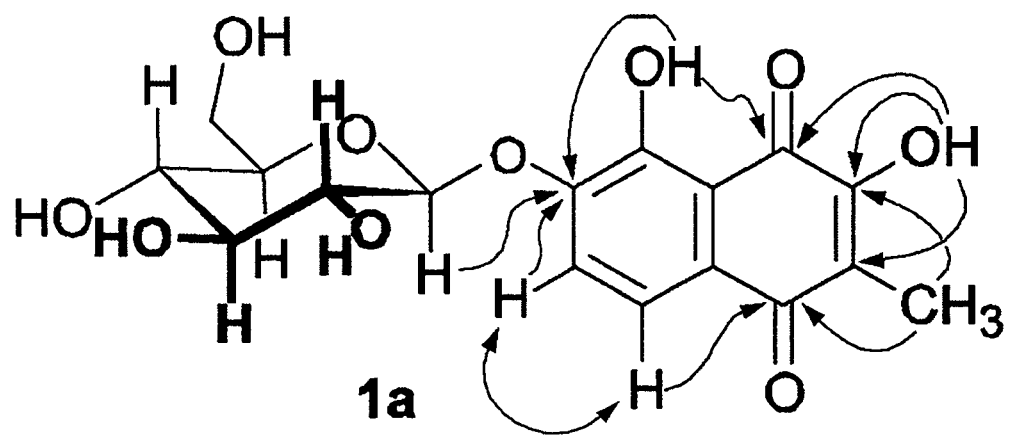

The invention is now further described by reference to the following examples which are intended to illustrate, not to limit the scope of the invention. All cited references are incorporated herein by reference.

EXAMPLE 1

Extraction and Isolation of the Compounds According to the Present Invention from Biological Material For the first time, a cell culture from tropical lianas of the family Dioncophyllaceae (preferably *Triphyophyllum peltatum* (Hutch. & Dalz.) Airy Shaw) was shown to produce the novel natural products Dioncoquinone A (1a) and B (1b). Furthermore, for the first time, a cell culture from tropical lianas of the family Ancistrocladaceae (preferably *Ancistrocladus abbreviatus* Airy Shaw) was shown to produce the novel natural products Ancistroquinone D (1c), E (1d), and F (1e). Under the cultivation conditions described below, these substances were released into the culture medium, as well as particularly accumulated in the biomass. The present species are two species of lianas which have been cultivated in Würzburg for many years (G. Bringmann, C. Schneider, F. Pokorny, H. Lorenz, H. Fleischmann, A. S. Sankaranarayanan, M. R. Almeida, T. R. Govindachari, L. Aké Assi, *Planta Med.* 1993, 59 (Suppl.), 623-624) and of which solid callus cultures have been established after cultivation under sterile conditions.

General Method for Establishing Solid Callus Cultures

It was possible to produce fresh seeds from the two mentioned species *Triphyophyllum peltatum* (Hutch. & Dalz.) Airy Shaw and *Ancistrocladus abbreviatus* Airy Shaw. Voucher specimens of both plant species have been deposited in the Herb. Bringmann, University of Würzburg [No. 2, 35, and 36 (*T. peltatum*) and No. 32 (*A. abbreviatus*)], and in the Centre National de Floristique, Abidjan.

From these seeds aseptic plant cultures were established (G. Bringmann, H. Rischer, J. Schlauer, L. Aké Assi, *Plant Cell Tissue Organ Cult.* 1999, 57, 71-73; G. Bringmann, J. Schlauer, K. Wolf, H. Rischer, U. Buschbom, A. Kreiner, F. Thiele, M. Duschek, L. Aké Assi, *Carniv. Pl. Newslett.* 1999, 28, 7-13), which served to establish axenic callus cultures whose cultivation and propagation were performed as described before (G. Bringmann, H. Rischer, J. Schlauer, L. Aké Assi, *Plant Cell Tissue Organ Cult.* 1999, 57, 71-73; G. Bringmann, H. Rischer, M. Wohlfarth, J. Schlauer, L. Aké Assi, *Phytochemistry* 2000, 53, 339-343).

After several transfers, the cultivation conditions for the calli from *Triphyophyllum peltatum* (Hutch. & Dalz.) Airy Shaw were modified.

The gelatinizing agent used (Gelrite) requires divalent ions (calcium and/or magnesium) in order to solidify. Plant cells also need these ions as nutrition elements, particularly in stress situations (such as the cultivation of plant cells in the artificially generated callus form). The strongly reduced concentration of the main nutrition elements in the culture medium led to a competition for calcium and magnesium between the cells and the gelatinizing agent, so that the medium liquefied already after a short culture period (less than 4 weeks) and the cultures sank in it. This resulted in an undersupply of calcium and magnesium ions for the cells and additionally in oxygen insufficiency due to the sinking. To avoid this and to induce the production of novel higher-oxygenated metabolites by an increase of the "oxygen pressure" due to the pronounced exposure of the calli to air, the concentration of calcium and magnesium ions was increased in a stepwise manner until the medium stayed stable even for longer culture periods. Under these conditions, the above-mentioned secondary metabolites according to the present invention were reliably produced by the plant cells.

Cultivation was carried out in 100-mL Erlenmeyer flasks on a modified MS medium (T. Murashige, T. Skoog, *Physiol. Plant.* 1962, 15, 473-497), whose content of the main nutrition elements was reduced to ⅕ (20%), with the exception of the calcium and magnesium concentration, whose ratio was reduced to ¼ (25%) of the original concentration. The modified medium had the following composition:

83.05 mg $L^{-1}$ $CaCl_2$
34.0 mg $L^{-1}$ $KH_2PO_4$
380 mg $L^{-1}$ $KNO_3$
45.135 mg $L^{-1}$ $MgSO_4$
330 mg $L^{-1}$ $NH_4NO_3$
27.80 mg $L^{-1}$ $FeSO_4 \times 7H_2O$
37.3 mg $L^{-1}$ $Na_2EDTA$
0.025 mg $L^{-1}$ $CoCl_2 \times 6H_2O$
0.025 mg $L^{-1}$ $CuSO_4 \times 5H_2O$
6.20 mg $L^{-1}$ $H_3BO_4$
0.83 mg $L^{-1}$ KI
16.90 mg $L^{-1}$ $MnSO_4 \times H_2O$
0.25 mg $L^{-1}$ $Na_2MoO_4 \times 2H_2O$
8.6 mg $L^{-1}$ $ZnSO_4 \times 7H_2O$
100 mg $L^{-1}$ myo-Inositol
0.5 mg $L^{-1}$ nicotinic acid
0.1 mg $L^{-1}$ thiamine×HCl
0.5 mg $L^{-1}$ pyridoxal×HCl
2.0 mg $L^{-1}$ glycine
30 000 mg $L^{-1}$ saccharose
2500 mg $L^{-1}$ Gelrite
2.0 mg $L^{-1}$ 6-BA (6-benzylaminopurine)
0.1 mg $L^{-1}$ NAA (1-naphthyl acetic acid)
(filled up to 1000 mL with distilled water)

The cultivation conditions for the callus culture from *Ancistrocladus abbreviatus* Airy Shaw were modified compared to the method known from the literature in the same way as described for the *Triphyophyllum* cultures. Cultivation was carried out in Petri dishes on modified MS medium (T. Murashige, T. Skoog, *Physiol. Plant.* 1962, 15, 473-497):

83.05 mg $L^{-1}$ $CaCl_2$
34.0 mg $L^{-1}$ $KH_2PO_4$
380 mg $L^{-1}$ $KNO_3$
45.135 mg $L^{-1}$ $MgSO_4$
330 mg $L^{-1}$ $NH_4NO_3$
27.80 mg $L^{-1}$ $FeSO_4 \times 7H_2O$
37.3 mg $L^{-1}$ $Na_2EDTA$
0.025 mg $L^{-1}$ $CoCl_2 \times 6H_2O$
0.025 mg $L^{-1}$ $CuSO_4 \times 5H_2O$
6.20 mg $L^{-1}$ $H_3BO_4$
0.83 mg $L^{-1}$ KI
16.90 mg $L^{-1}$ $MnSO_4 \times H_2O$
0.25 mg $L^{-1}$ $Na_2MoO_4 \times 2H_2O$
8.6 mg $L^{-1}$ $ZnSO_4 \times 7H_2O$
100 mg $L^{-1}$ myo-Inositol
0.5 mg $L^{-1}$ nicotinic acid
0.1 mg $L^{-1}$ thiamine×HCl
0.5 mg $L^{-1}$ pyridoxal×HCl
2.0 mg $L^{-1}$ glycine
30 000 mg $L^{-1}$ saccharose
2500 mg $L^{-1}$ Gelrite
0.5 mg $L^{-1}$ 6-BA (6-benzylaminopurine)
0.5 mg $L^{-1}$ 2,4-D (2,4-dichlorophenoxyacetic acid)
0.5 mg $L^{-1}$ NAA (1-naphthylacetic acid)
(filled up to 1000 mL with distilled water)

The culture can also be based on other media having similar compositions, such as LS medium (E. M. Linsmaier, F. Skoog, *Physiol. Plantarum* 1965, 18, 100-127), wherein the concentration of the main nutrition elements is reduced and adjusted to the above-listed compositions.

The pH values of the culture media were adjusted to 5.8 using NaOH and HCl, respectively. Sterilization was carried out by 20-min autoclavation at 121° C. and 210 kPa. The cultures were kept under light with a 14-h photoperiod at 51 $\mu M$ $m^{-2}$ $s^{-1}$ photosynthetically active radiation (Osram L58W/77 FLUORA in combination with Osram L58W/954 Lumilux de luxe Daylight) at 24±2° C. However, higher and lower temperatures or radiation values can be used as well. The calli of *Triphyophyllum peltatum* were transferred every 8 weeks to fresh solid medium, whereas the callus cultures of *Ancistrocladus abbreviatus* were transferred every 10 weeks.

The modified conditions led to a fast growth of the cells due to better supply and significantly improved the physical properties of the medium without harming the cultures with a too high concentration of calcium ions. Thus, the liquefaction of the culture medium and the oxygen insufficiency of the cell cultures associated therewith, which had been observed under the conditions used so far, were avoided even for longer culture periods. The calli showed an about 20% increased growth rate and a significantly increased ratio of the substances according to the present invention in the overall spectrum of metabolites.

Isolation of the Compounds According to the Present Invention

The calli of several cell cultures were separated from the medium, lyophilized, grounded and extracted with 3×100 mL of a $CH_2Cl_2$:$CH_3OH$ (1:1) mixture for 72 hours under stirring. Subsequently, the cell biomass was removed by filtration, and the resulting extracts were concentrated in vacuo to yield a crude residue. The compounds contained therein were then isolated via preparative HPLC:

Column: Waters SymmetryPrep C18, 19×300 mm
Eluent: acetonitrile+0.05% TFA, water+0.05% TFA (trifluoroacetic acid)
Gradient: 5% acetonitrile to 70% acetonitrile in 30 min
Flow: 10 mL $min^{-1}$
Detection wavelength: 220 nm Dioncoquinone A (1a) eluted after 15.4 min, Dioncoquinone B (1b) eluted after 21.6 min, Ancistroquinone D (1c) eluted after 28.8 min, Ancistroquinone E (1d) eluted after 29.3 min, and Ancistroquinone F (1e) eluted after 26.0 min. The corresponding fractions were collected and concentrated in vacuo to yield a crude residue. This yielded 18.5 mg of Dioncoquinone A (1a), 9.6 mg of Dioncoquinone B (1b), 5.2 mg of Ancistroquinone D (1c), 4.5 mg of Ancistroquinone E (1d), and 6.4 mg of Ancistroquinone F (1e) as amorphous solids.

Spectroscopic Data and Structural Elucidation of the Isolated Compounds

A) Dioncoquinone A (1a; 3,5,6-trihydroxy-2-methyl-1,4-naphthoquinone-6-O-β-glucoside Melting point (m.p.): 189° C. (methanol, $CH_3OH$);
Specific optical rotation: $[\alpha]_D^{20}$=67.2 (c=0.05, DMSO:$CH_3OH$ 1:1);
UV ($CH_3OH$): $\lambda_{max}$ [nm]=206 (1.72), 255 (1.37), 295 (0.75), 413 (0.34);
IR (KBr): $\tilde{\nu}$ $[cm^{-1}]$=3405 (br, m), 2923 (m), 2853 (w), 1638 (s), 1458 (m), 1365 (w), 1262 (m), 1074 (s), 842 (w), 641 (w);
$^1$H-NMR (600 MHz, DMSO-$d_6$): δ [ppm]=1.91 (s, 3H, $CH_3$-2), 3.18 (d, $^3J$=8.5 Hz, 1H, H-4'), 3.29-3.31 (m, 1H, H-5'), 3.30-3.32 (m, 1H, H-2'), 3.38 (dd, $^3J$=7.6 Hz, $^4J$=1.9 Hz, 1H, H-3'), 3.47 (dd, $^2J$=11.9 Hz, $^3J$=5.8 Hz, 1H, H-6'), 3.68 (dd, $^2J$=11.9 Hz, $^3J$=1.9 Hz, 1H, H-6'), 5.07 (d, $^3J$=7.4 Hz, 1H, H-1'), 7.43 (d, $^3J$=8.6 Hz, 1H, H-7), 7.45 (d, $^3J$=8.6 Hz, 1H, H-8), 10.89 (s, 1H, OH-3), 11.42 (s, 1H, OH-5);
$^{13}$C-NMR (150 MHz, DMSO-$d_6$): δ [ppm]=8.7 (C-11), 60.4 (C-6'), 69.4 (C-4'), 73.0 (C-5'), 76.5 (C-2'), 77.2 (C-3'), 99.8 (C-1'), 114.0 (C-10), 118.8 (C-7), 119.7 (C-8), 120.7 (C-2), 125.0 (C-9), 150.0 (C-6), 150.3 (C-5), 155.1 (C-3), 183.4 (C-4), 184.4 (C-1);
MS (EI, 70 eV): m/z (%) 220.1 (100) $[M-Glc]^+$, 192.1 (24) $[M-Glc-H_2O]^+$, 163.1 (19), 146.1 (25);
$C_{17}H_{17}O_{10}$ (HRMS): calc. 381.0827, m/z 381.0827.
(see FIG. 1)

TABLE 1

NMR data of Dioncoquinone A (1a) (in DMSO-$d_6$; 600 MHz)

| Position | $^{13}$C [ppm] | $^1$H [ppm] | HMBC | COSY ($J_{HH}$ [Hz]) |
|---|---|---|---|---|
| 1 | 184.4 | | | |
| 2 | 120.7 | | | |
| 3 | 155.1 | | | |
| 4 | 183.4 | | | |
| 5 | 150.3 | | | |
| 6 | 150.0 | | | |
| 7 | 118.8 | 7.43, d | 5, 6, 9 | 8 (8.6) |
| 8 | 119.7 | 7.45, d | 1, 6, 10 | 7 (8.6) |
| 9 | 125.0 | | | |
| 10 | 114.0 | | | |
| 11 | 8.7 | 1.91, s | 1, 2, 3 | |
| 1' | 99.8 | 5.07, d | 6, 2', 3' | 2' (7.4) |
| 2' | 76.5 | 3.30-3.32, m | 1', 2' | |
| 3' | 77.2 | 3.38, dd | 1', 5' | 2' (7.6), 5' (1.9) |
| 4' | 69.4 | 3.18, d | 2', 3', 6' | 5' (8.5) |
| 5' | 73.0 | 3.29-3.31, m | 1', 3', 6' | |
| 6' | 60.4 | α 3.47, dd | 3', 4' | 5' (5.8), 6'β (11.9) |
| | | β 3.68, dd | 3', 4' | 5' (1.9), 6'α (11.9) |

In accordance with the empirical formula $C_{17}H_{18}O_{10}$ derived from high-resolution mass spectrometry, in the $^{13}$C-NMR spectrum of Dioncoquinone A 17 signals were observed. By analysis of the HMBC, HMQC, and COSY spectra, 11 carbon atoms were assigned to a 2-methyl-1,4-naphthoquinone framework. A threefold oxygenation of this basic scaffold was indicated by the presence of three signals of phenolic and, thus, quaternary carbon atoms in the $^{13}$C-NMR spectrum. Their assignment to positions 3, 5, and 6 (see FIG. 1A) was possible on the basis of the HMBC interactions 3-OH→C-4, 3-OH→C-2, and 5-OH→C-4, 5-OH→C-6, respectively, since the correlation 8-H→C-1 indicated that the remaining two neighboring aromatic protons are bound to C-7 and C-8 (FIG. 1B). A glucose group was identified as an additional structural element on the basis of the characteristic shifts of the signals in $^1$H- and $^{13}$C-NMR and by COSY and HMBC interactions. An HMBC interaction of the anomeric proton 1'-H with C-6 suggested the linkage of the glucose group to the aromatic ring of the naphthoquinone via C-1' and C-6 of the naphthoquinone, and the presence of a β-linkage was shown by the characteristically large biaxial coupling constant $^3J_{HH}$ of 7.4 Hz.

The only proposed structure in agreement with all mentioned HMBC interactions and the empirical formula $C_{17}H_{18}O_1$ is the naphthoquinone glucoside with the formula 1a. According to its isolation from the plant family Dioncophyllaceae and to its quinoide structure, the new natural product was named Dioncoquinone A.

In order to confirm the absolute configuration of the glucose group, the natural product was treated with methanolic HCl. This led to complete deglucosidation, delivering D-glucose, whose physical, chiroptical, and spectroscopic properties were identical to those of a commercially available sample.

B) Dioncoquinone B (1b; 3,5,6-trihydroxy-2-methyl-1,4-naphthoquinone)

Figure 2:
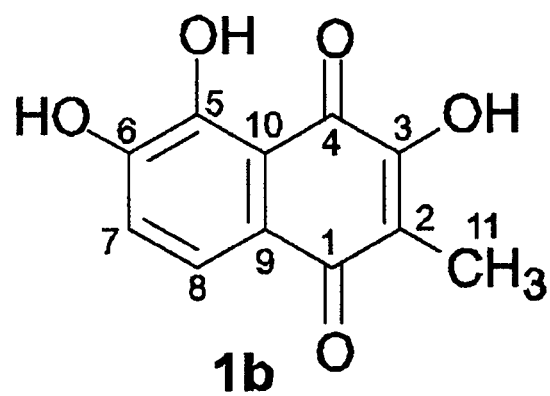
FIG. 2 shows Dioncoquinone B (1b) with C-atoms numbered 1-11 (A) as well as a scheme illustrating the derivatization of 1b to 1f using diazomethane with $^1H,^1H$—COSY interactions relevant for the structural elucidation indicated by double arrows (B)
Figure 2:
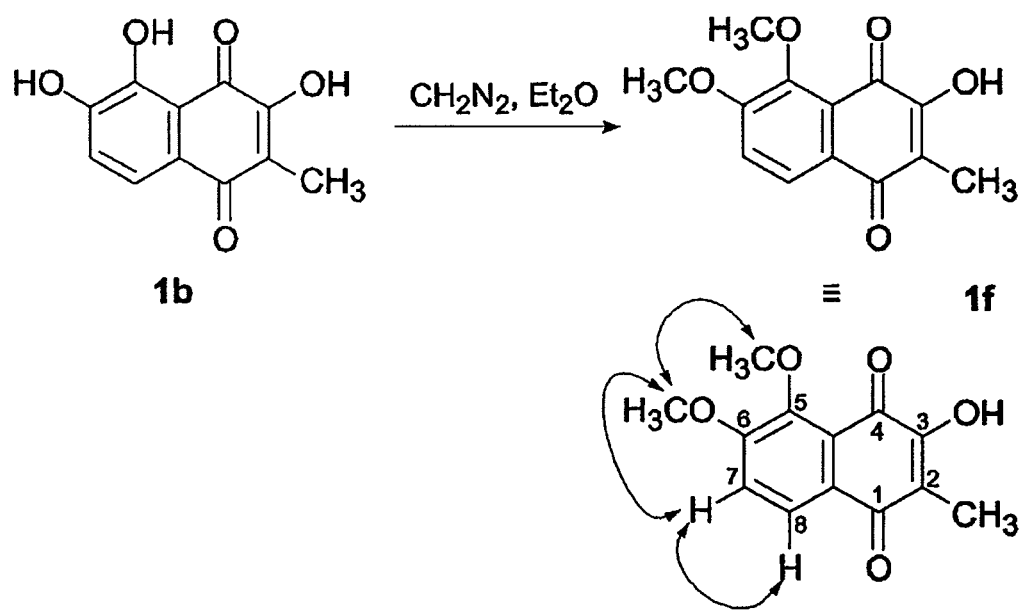

M.p.: 218° C. (chloroform-$d_3$);
UV ($CH_3OH$): $\lambda_{max}$ [nm]=215 (1.57), 269 (1.12), 317 (0.67), 416 (0.33);
IR (KBr): $\tilde{v}$ [$cm^{-1}$]=3408 (br, m), 2922 (m), 2853 (w), 1618 (s), 1459 (m), 1297 (s), 1209 (w), 1105 (m), 430 (w);
$^1$H-NMR (400 MHz, $CDCl_3$): δ [ppm]=2.09 (s, 3H, $CH_3$-2), 6.03 (s, 1H, OH-6), 7.02 (s, 1H, OH-3), 7.18 (d, $^3J$=8.3 Hz, 1H, H-7), 7.64 (d, $^3J$=8.3 Hz, 1H, H-8), 11.20 (s, 1H, OH-5);
$^{13}$C-NMR (100 MHz, $CDCl_3$): δ [ppm]=8.9 (C-11), 113.4 (C-10), 120.4 (C-7), 121.3 (C-8), 124.3 (C-9), 126.5 (C-2), 142.8 (C-5), 148.0 (C-6), 149.3 (C-3), 184.7 (C-4), 185.0 (C-1);
MS (EI, 70 eV): m/z (%) 220.1 (46) $[M]^+$, 192.1 (15) $[M-H_2O]^+$, 163.1 (13), 146.1 (12);
$C_{11}H_7O_5$ (HRMS): calc. 219.0299, m/z 219.0203.
(see FIG. 2)

TABLE 2

NMR data of Dioncoquinone B (1b) (in MeOH-$d_4$; 600 MHz)

| Position | $^{13}$C [ppm] | $^1$H [ppm] | HMBC | COSY ($J_{HH}$ [Hz]) |
|---|---|---|---|---|
| 1 | 185.0 | | | |
| 2 | 126.5 | | | |
| 3 | 149.3 | | | |
| 4 | 184.7 | | | |
| 5 | 142.8 | | | |
| 6 | 148.0 | | | |
| 7 | 120.4 | 7.18, d | 5, 6, 9 | 8 (8.6) |
| 8 | 121.3 | 7.64, d | 1, 5, 6, 10 | 7 (8.6) |
| 9 | 124.3 | | | |
| 10 | 113.4 | | | |
| 11 | 8.9 | 2.09, s | 1, 2, 3 | |

The analysis of all spectroscopic and physical data of compound 1b revealed the same 2-methyl-3-hydroxy-1,4-naphthoquinone scaffold as the one of Dioncoquinone A (FIG. 2A). Indeed, co-chromatography identified the novel compound as the aglycon of Dioncoquinone A. Since the additional hydroxy proton (as compared to the substitution pattern of Dioncoquinone A) did not deliver any signals in the 2D NMR spectra due to exchange phenomena, an O-methylation using diazomethane was carried out in order to confirm the constitution of 1b. Twofold O-methylation of the phenolic OH-groups on the aromatic ring led to the dimethyl derivative 1f (FIG. 2B). The position of the methyl groups, thus introduced, was determined by HMBC and NOESY experiments, and the NOESY interactions 5-$OCH_3$↔ 6-$OCH_3$↔ 7-H ↔ 8-H unequivocally confirmed the accuracy of the proposed structure.

C) Ancistroquinone D (1c; 3,8-dihydroxy-5,6-dimethoxy-2-methyl-1,4-naphthoquinone)

Figure 3:
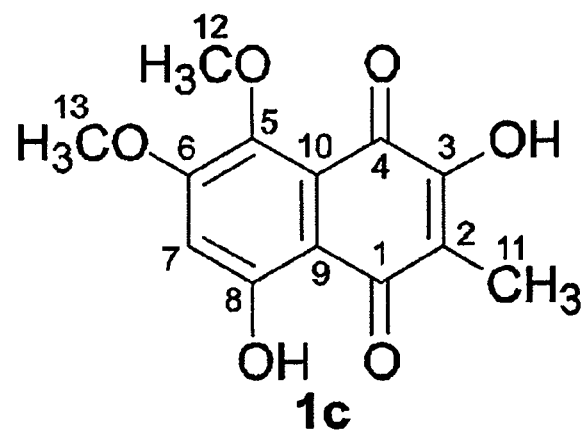
FIG. 3 shows Ancistroquinone D (1c) with C-atoms numbered 1-13 (A) as well as HMBC (single arrows) and $^1H,^1H$—COSY (double arrows) interactions relevant for the structural elucidation (B)
Figure 3:
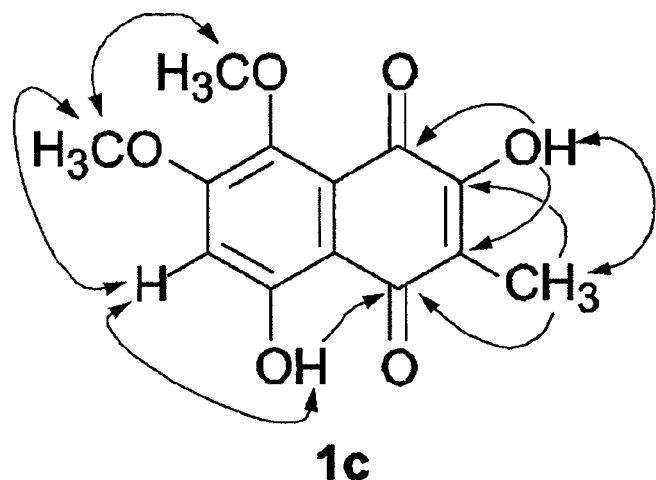

M.p.: 218-220° C. (dichloromethane);
UV ($CH_3OH$): $\lambda_{max}$ [nm]=215 (1.02), 261 (0.58), 305 (0.41), 411 (0.23);
IR (KBr): $\tilde{v}$ [$cm^{-1}$]=3349 (m), 2925 (w), 2854 (w), 1650 (s), 1609 (s), 1478 (m), 1426 (m), 1392 (m), 1334 (m), 1291 (m), 1260 (m), 1149 (s), 1022 (m), 861 (w), 461 (w);
$^1$H-NMR (600 MHz, $CDCl_3$): δ [ppm]=2.07 (s, 3H, $CH_3$-2), 3.89 (s, 3H, $OCH_3$-5), 3.94 (s, 3H, $OCH_3$-6), 6.70 (s, 1H, H-7), 7.64 (s, 1H, OH-3), 13.44 (s, 1H, OH-8);
$^{13}$C-NMR (150 MHz, $CDCl_3$): δ [ppm]=8.1 (C-11), 56.4 (C-13), 61.2 (C-12), 106.6 (C-9), 107.2 (C-7), 118.7 (C-2), 120.6 (C-10), 145.9 (C-5), 153.7 (C-3), 160.0 (C-6), 160.9 (C-8), 179.1 (C-4), 189.5 (C-1);
MS (CI, $CH_4$): m/z (%) 265.1 (100) $[M+H]^+$;
$C_{13}H_{13}O_6$ (HRMS): calc. 265.0706, m/z 265.0709.
(see FIG. 3)

TABLE 3

NMR data of Ancistroquinone D (1c) (in $CDCl_3$; 600 MHz)

| Position | $^{13}$C [ppm] | $^1$H [ppm] | HMBC | NOESY | COSY ($J_{HH}$ [Hz]) |
|---|---|---|---|---|---|
| 1 | 189.5 | | | | |
| 2 | 118.7 | | | 11 | |
| 3 | 153.7 | | | | |
| 4 | 179.1 | | | | |
| 5 | 145.9 | | | | |
| 6 | 160.0 | | | | |
| 7 | 107.2 | 6.70 | 1, 5, 8, 9 | 8 | |
| 8 | 160.9 | | | 7 | |
| 9 | 106.6 | | | | |
| 10 | 120.6 | | | | |
| 11 | 8.1 | 2.07, s | 1, 2, 3 | 2 | |
| 12 | 61.2 | 3.89, s | 5 | 13 | |
| 13 | 56.4 | 3.94, s | 6 | 12 | |

The NMR spectra of Ancistroquinone D (1c) exhibited a high similarity to those of 1b and 1f. Again a 3-hydroxy-2-methyl-1,4-naphthoquinone was found, and in agreement with the empirical formula $C13H_{13}O_6$ derived from high-resolution mass spectrometry, the $^{13}$C-NMR spectrum of Ancistroquinone D showed 4 signals of quaternary carbon atoms at 160.9, 160.0, 153.7, and 145.9 ppm, which supported a fourfold oxygenated 1,4-naphthoquione (FIG. 3A). The fact that two of these O-functionalities are methylated, was revealed by two three-proton signals in $^1$H-NMR, and the NOE correlations 5-$OCH_3$ ↔ 6-$OCH_3$ ↔ 7-H allowed the assignment of these methoxy groups to C-5 and C-6 (FIG. 3B). That the second free hydroxy group was positioned at C-8 was shown by the HMBC interaction 8-OH→C-1 as well as the NOE correlation 8-OH ↔ 7-H. The sum of all above mentioned 2D NMR interactions led to the structural assignment of the new compound as 1c.

D) Ancistroquinone E (1d; 3,5,8-trihydroxy-2-methyl-6,7-methylendioxy-1,4-naphthoquinone)

Figure 4:
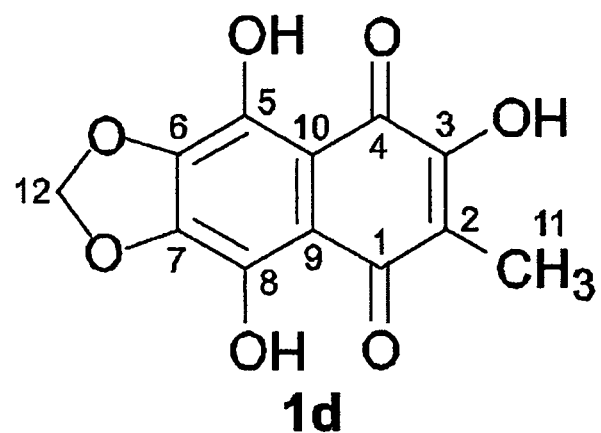
FIG. 4 shows Ancistroquinone E (1d) with C-atoms numbered 1-12 (A) as well as HMBC (single arrows) and $^1H,^1H$—COSY (double arrows) interactions relevant for the structural elucidation (B)
Figure 4:
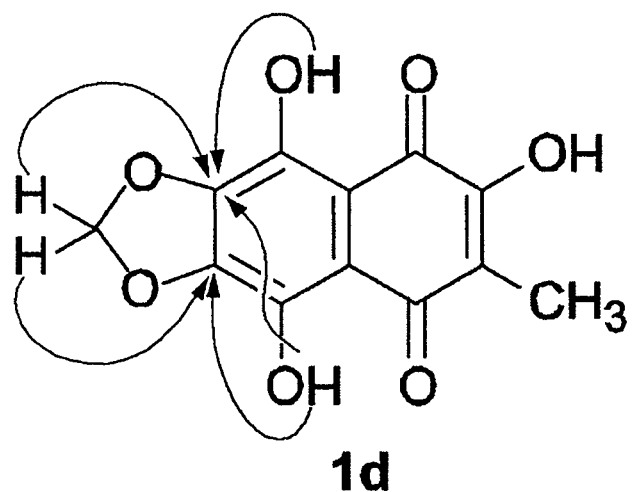

M.p.: 242° C. (sublimation, dichloromethane);
UV ($CH_3OH$): $\lambda_{max}$ [nm]=233 (0.89), 263 (0.82), 343 (0.39), 460 (0.32) nm;
IR (KBr): $\tilde{v}$ [$cm^{-1}$]=3384 (br, m), 2961 (m), 2923 (s), 2853 (m), 1654 (s), 1560 (m), 1459 (m), 1262 (m), 1098 (s), 1027 (m), 801 (m);
$^1$H-NMR (600 MHz, $CDCl_3$): δ [ppm]=2.07 (s, 3H, $CH_3$-2), 6.25 (s, 2H, H-12), 11.48 (s, 1H, OH-5), 12.94 (s, 1H, OH-8);
$^{13}$C-NMR (150 MHz, $CDCl_3$): δ [ppm]=8.1 (C-11), 104.5 (C-12), 107.8 (C-10), 109.0 (C-9), 120.8 (C-2), 140.8 (C-7), 144.4 (C-5), 144.6 (C-6), 144.9 (C-8), 153.9 (C-3), 180.9 (C-4), 188.7 (C-1);

MS (EI, 70 eV): m/z (%) 264.0 (100) [M]$^+$, 236.0 (44), 149 (33);
$C_{12}H_8O_7$ (HRMS): calc. 264.0273, m/z 264.0266.
(see FIG. 4)

TABLE 4

NMR data of Ancistroquinone E (1d) (in CDCl$_3$; 600 MHz)

| Position | $^{13}$C [ppm] | $^1$H [ppm] | COSY ($J_{HH}$ [Hz]) | HMBC |
|---|---|---|---|---|
| 1 | 188.7 | | | |
| 2 | 120.8 | | | |
| 3 | 153.9 | | | |
| 4 | 180.9 | | | |
| 5 | 144.4 | | | |
| 6 | 144.6 | | | |
| 7 | 140.8 | | | |
| 8 | 144.9 | | | |
| 9 | 109.0 | | | |
| 10 | 107.8 | | | |
| 11 | 8.1 | 2.07, s | | 1, 2, 3 |
| 12 | 104.5 | 6.25, s | | 6, 7 |

Again, the NMR spectra showed a 3-hydroxy-2-methyl-1,4-naphthoquinone framework. Strikingly, the $^1$H-NMR showed a two-proton singlet at 6.25 ppm besides the two drastically low-field shifted signals (12.94 and 11.48 ppm) of the chelated hydroxy groups in positions 5 and 8 (FIG. 4A). Several HMBC interactions proved this signal to correspond to a methylenedioxy group bridging C-6 and C-7 (FIG. 4B). In agreement with the empirical formula $C_{12}H_8O_7$ derived from high-resolution mass spectrometry, the structure 1d was assigned to the substance.

E) Ancistroquinone F (1e; 3-hydroxy-5-methoxy-2-methyl-6,7-methylenedioxy-1,4-naphthoquinone)

Figure 5:
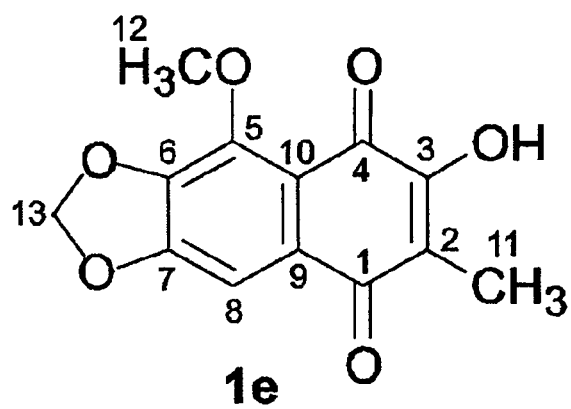
FIG. 5 shows Ancistroquinone F (1e) with C-atoms numbered 1-13 (A) as well as HMBC (single arrows) interactions relevant for the structural elucidation (B)
Figure 5:
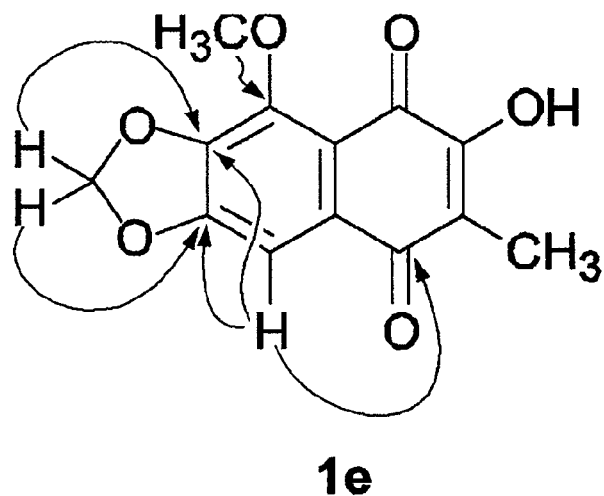

M.p.: 220° C. (decomposition, dichloromethane);
UV (CH$_3$OH): $\lambda_{max}$ [nm]=220 (1.13), 271 (1.06), 319 (0.53), 377 (0.17);
IR (KBr): $\tilde{\nu}$ [cm$^{-1}$]=3412 (br, m), 2924 (s), 2853 (w), 1734 (m), 1638 (s), 1584 (m), 1347 (m), 1245 (m), 1096 (m), 1033 (m), 747 (w);
$^1$H-NMR (400 MHz, CDCl$_3$): δ [ppm]=2.02 (s, 3H, CH$_3$-2), 4.14 (s, 3H, OCH$_3$-5), 6.11 (s, 2H, H-13), 7.39 (s, 1H, H-8);
$^{13}$C-NMR (100 MHz, CDCl$_3$): δ [ppm]=8.4 (C-11), 60.6 (C-12), 102.5 (C-13), 103.1 (C-8), 116.2 (C-10), 117.1 (C-2), 131.8 (C-9), 140.6 (C-6), 144.4 (C-5), 153.4 (C-3), 154.0 (C-7), 178.9 (C-4), 183.6 (C-1);
MS (EI, 70 eV): m/z (%) 262.0 (20) [M]$^+$, 149.1 (100);
$C_{13}H_9O_6$ (HRMS): calc. 261.0404, m/z 261.0402.
(see FIG. 5)

TABLE 5

NMR data of Ancistroquinone F (1e) (in CDCl$_3$; 400 MHz)

| Position | $^{13}$C [ppm] | $^1$H [ppm] | HMBC | COSY ($J_{HH}$ [Hz]) |
|---|---|---|---|---|
| 1 | 183.6 | | | |
| 2 | 117.1 | | | |
| 3 | 153.4 | | | |
| 4 | 178.9 | | | |
| 5 | 144.4 | | | |
| 6 | 140.6 | | | |
| 7 | 154.0 | | | |
| 8 | 103.1 | 7.39 | 1, 6, 7, 10 | |
| 9 | 131.8 | | | |
| 10 | 116.2 | | | |
| 11 | 8.4 | 2.02, s | 1, 2, 3 | |
| 12 | 60.6 | 4.14, s | 5 | |
| 13 | 102.5 | 6.11, s | 6, 7 | |

The NMR spectra of Ancistroquinone F (1e) exhibited high similarity to those of 1d. Again, a methylenedioxy acetal was found, which bridged carbon atoms 6 and 7 of a 3-hydroxy-2-methyl-1,4-naphthoquinone (confirmed by HMBC interactions with C-6 and C-7, FIG. 5). In contrast to 1d, the aromatic ring was only threefold O-substituted, and HMBC interactions with C-1, C-6, and C-7 showed that the only aromatic proton was bound to C-8. The hydroxy function on C-5 was methylated, and in agreement with the nomenclature used above, the new compound 1e was named Ancistroquinone F.

EXAMPLE 2

Chemical Synthesis of 1,4-naphthoquinones Having the General Formula 1

Figure 6:
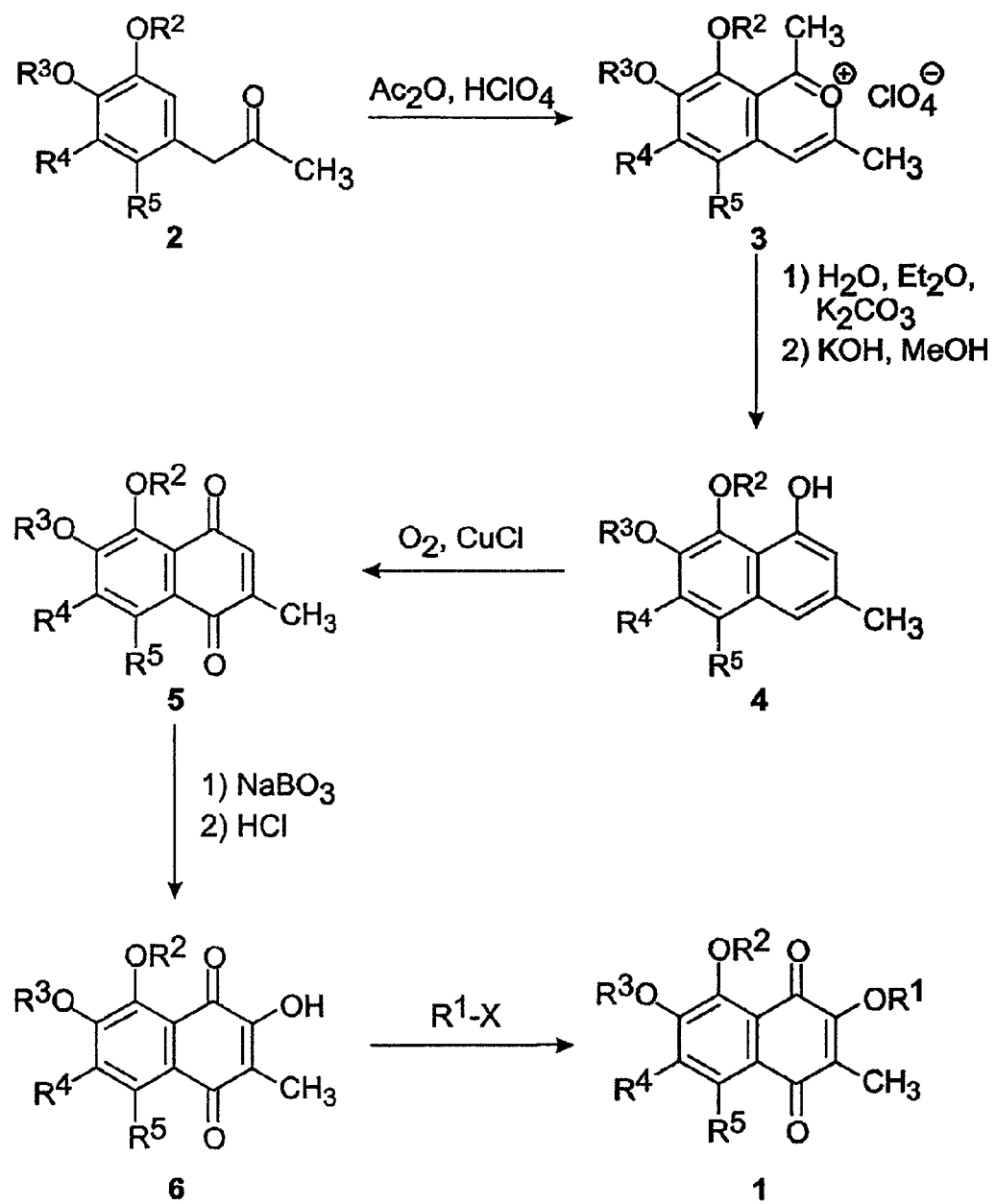
FIG. 6 shows a scheme illustrating the general synthesis of 1,4-naphthoquinones having the general formula 1.

For the chemical synthesis of 1,4-naphthoquinones having the general formula 1, the synthesis pathway shown in FIG. 6 can be used. Starting with the arylpropan-2-one of the general formula 2, the benzopyrylium salt 3 can be prepared, e.g. by treatment with acetic acid anhydride and perchloric acid (analogous to: G. Bringmann, J. R. Jansen, Liebigs Ann. Chem. 1985, 2116-2125). This salt can be further converted into the naphthalene derivative 4 by a base or acid catalyzed ring-opening/ring-closing sequence (analogous to: G. Bringmann, Liebigs Ann. Chem. 1985, 2126-2134). After oxidation, resulting in the 1,4-naphthoquinone having the general formula 5 (e.g. using O$_2$ and CuCl, analogous to: M. Yamashita, M. Kaneko, A. Iida, H. Tokuda, K. Nishimura, Bioorg. Med. Chem. Lett. 2007, 17, 6417-6420), the hydroxy function at C-3 might be introduced by epoxidation of the electron-deficient double bond of C-2/C-3 followed by opening of the epoxide resulting in the additionally hydroxylated naphthoquinones of the general formula 6 (analogous to: K. Ogihara, R. Yamashiro, M. Higa, S. Yogi, Chem. Pharm. Bull. 1997, 45, 437-445). The (optional) introduction of group R$^1$ at the hydroxy function of C-3 will complete the synthesis of the compounds having the general formula 1 according to the present invention.

EXAMPLE 3

Biological Activities of the Compounds According to the Present Invention

A) Activities Against Parasites of the Genus Leishmania
Amastigote forms of Leishmania donovani (MHOM-ET-67/L82 strain) were grown in axenic culture at 37° C. and pH 5.4 in SM medium (I. Cunningham, J. Protozool. 1977, 24, 325-329) supplemented with 10% fetal bovine serum. For the assay, amastigote forms were seeded into a microtiter plate containing two concentrations of each substance to be tested. After 72 h the dye Alamar Blue (Resazurin) was added to each culture, and the plate was incubated for two more hours. Fluorescence at 536/588 nm was measured using a microtiter plate fluorometer, and the fluorescence signal of each culture treated with a substance was compared to the fluorescence signal of untreated control cultures. The antileishmanial drug miltefosine served as a positive control.

TABLE 6

Antiinfective effect against *Leishmania donovani*

| Compound | Inhibition of cell growth (%) at c = 4.8 µg/ml | Inhibition of cell growth (%) at c = 0.8 µg/ml |
|---|---|---|
| Dioncoquinone A (1a) | 80.3 | 49.6 |
| Dioncoquinone B (1b) | 87.6 | 79.2 |
| Ancistroquinone D (1c) | 31.7 | 11.4 |
| Ancistroquinone E (1d) | 30.5 | 19.6 |
| Ancistroquinone F (1e) | 28.6 | 0.3 |
| Miltefosine (Control) | — | 53.0 (c = 0.22 µg/ml) |

As can be seen in Table 6, all exemplary compounds according to the present invention showed good, Dioncoquinone A (1a) and Dioncoquinone B (1b) even excellent activity against *Leishmania donovani*. Dioncoquinone B (1b) seems to be particularly suitable as a lead structure, which can be further chemically derivatized.

B) Antitumoral Activities

Figure 7:
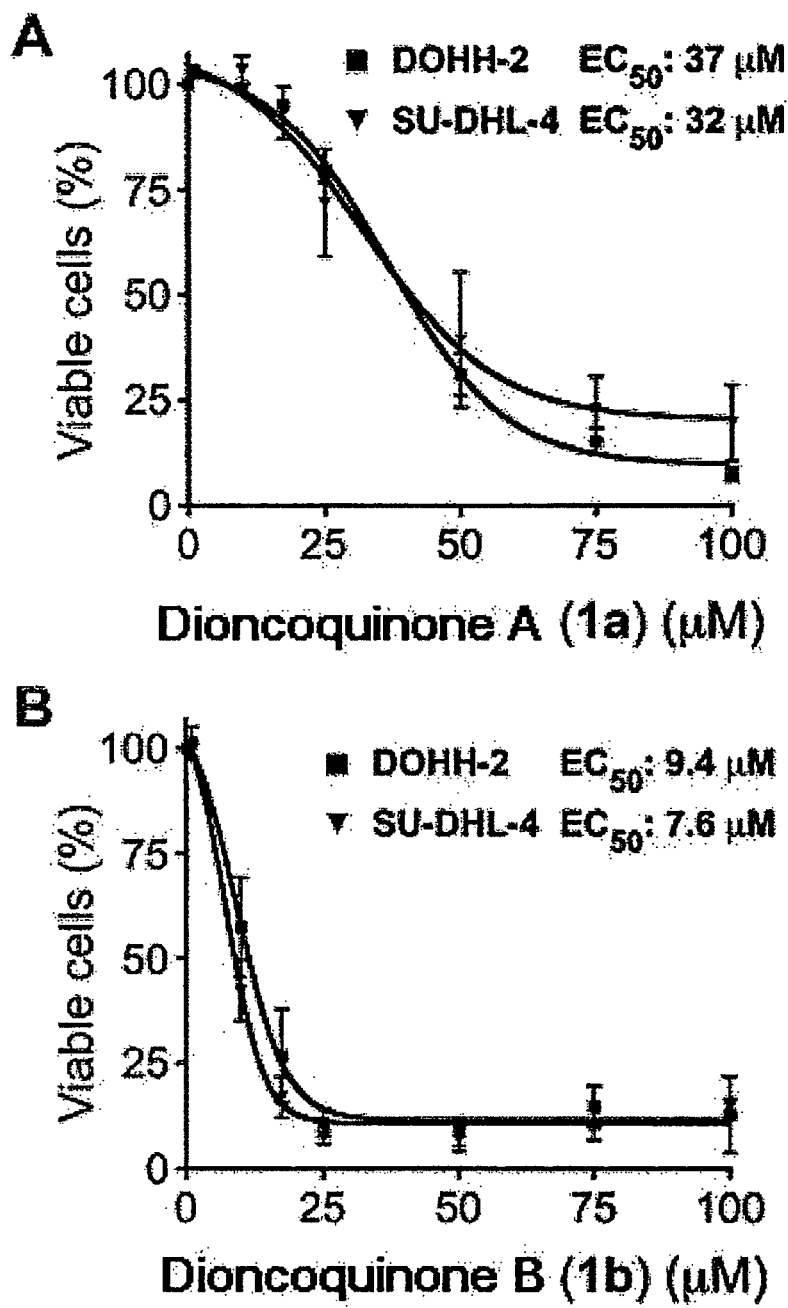
FIG. 7 shows curves of cell viability in response to various concentrations of Dioncoquinone A (1a) (A) and Dioncoquinone B (1b) (B) for the B cell lymphoma cell lines DOHH-2 and SU-DHL-4; error bars indicate the range of values derived from three different experiments.
Figure 8:
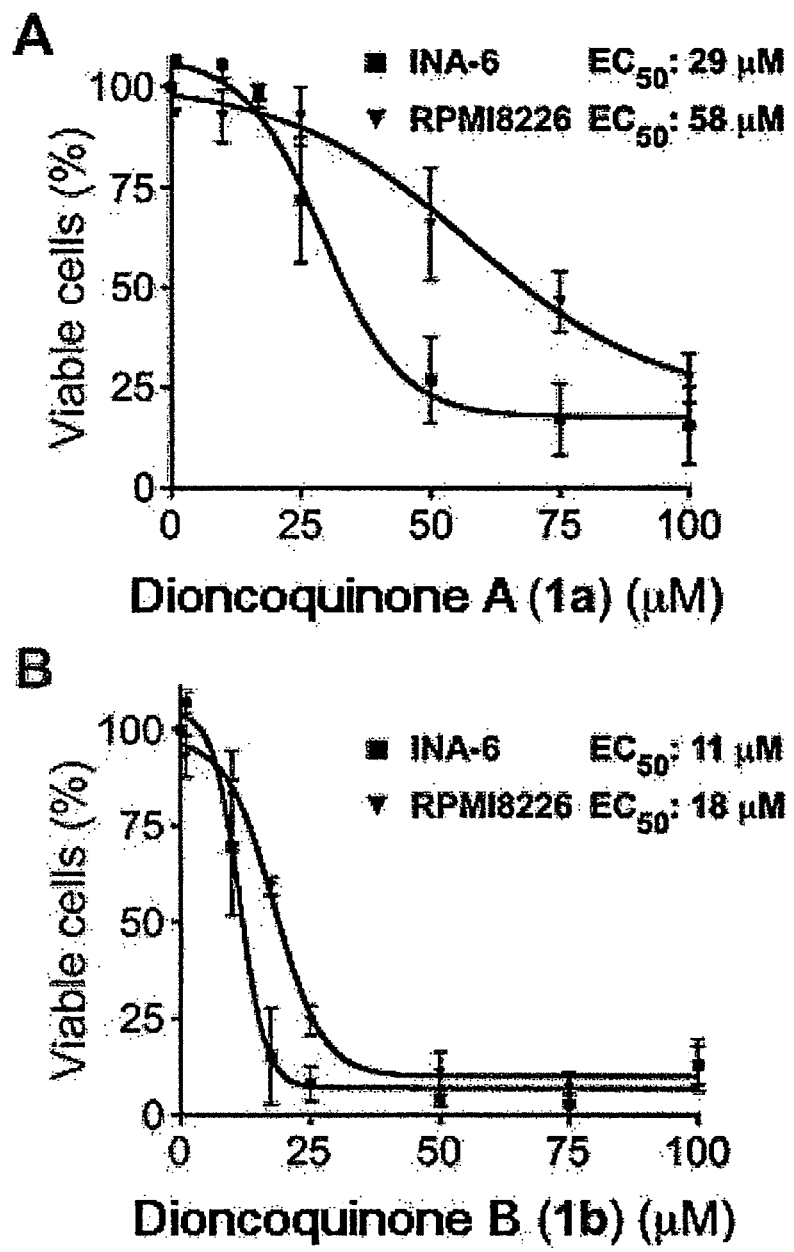
FIG. 8 shows curves of cell viability in response to various concentrations of Dioncoquinone A (1a) (A) and Dioncoquinone B (1b) (B) for the multiple myeloma cell lines INA-6 and RPMI8226; error bars indicate the range of values derived from three different experiments.
Figure 9:
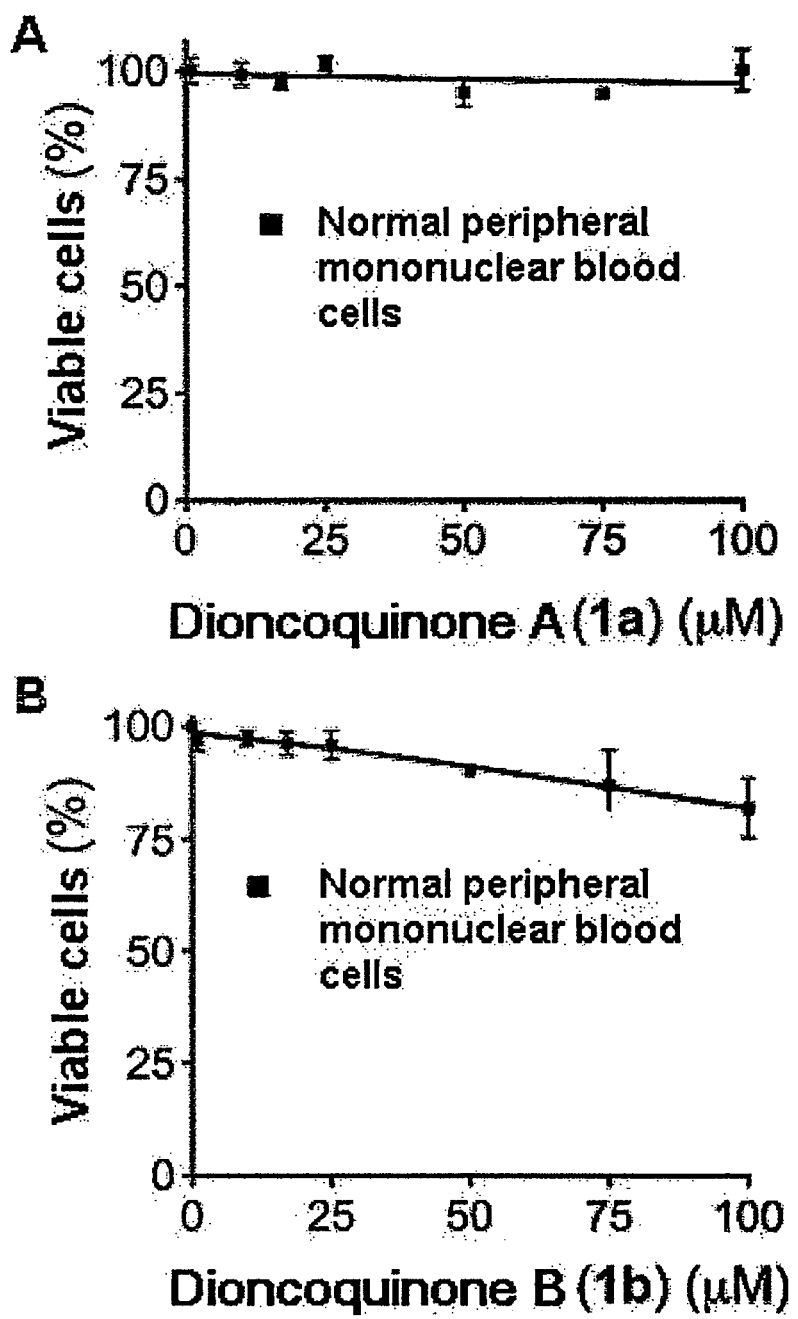
FIG. 9 shows curves of cell viability in response to various concentrations of Dioncoquinone A (1a) (A) and Dioncoquinone B (1b) (B) for normal (i.e. non-malignant) peripheral mononuclear blood cells; error bars indicate the range of values derived from three different experiments.

The antitumoral activity of the compounds Dioncoquinone A (1a) and B (1b) was demonstrated using two cell lines each of two different B cell malignancies, B cell lymphoma and multiple myeloma (INA-6, RPMI8226, SU-DHL-4, DOHH-2). The selectivity of this activity was shown by further experiments using normal peripheral mononuclear blood cells, whose growth was not significantly inhibited within the therapeutic concentration range. Both cell lines of aggressive B cell lymphoma (DOHH-2, SU-DHL-4) and the multiple myeloma cell line RPMI8226 were obtained from the German Collection of Microorganisms and Cell Cultures (DSMZ) (ACC 47, ACC 495, and ACC 402, Braunschweig, Germany). The cultivation of the multiple myeloma cell line INA-6 had been previously described (R. Burger, A. Guenther, F. Bakker, M. Schmalzing, S. Bernand, W. Baum, B. Duerr, G. M. Hocke, H. Steininger, E. Gebhart, M. Gramatzki, *Hematol. J.* 2001, 2, 42-53). Normal mononuclear blood cells from the peripheral blood of two healthy donors were isolated by Ficoll-Hypaque density gradient centrifugation. To assess the percentage of apoptotic and viable cell fractions, a human annexin V-FITC/PI staining kit (Bender MedSystems, Vienna, Austria) was used. Cells (inoculation: 50000 cells $mL^{-1}$; incubation: 72 h) were washed in PBS, incubated for 10 min in 100 ml binding buffer (10 mM HEPES/NaOH, pH 7.4, 140 mM NaCl, 2.5 mM $CaCl_2$) containing 2.5 ml annexin V-FITC mix and 1 mg/ml propidium iodide (PI), subsequently diluted with 300 ml binding buffer and analyzed by flow cytometry (FACSCalibur/CELLQuest; Becton Dickinson, Heidelberg, Germany). Early apoptosis is characterized by a positive annexin V-FITC staining. Cells in a late apoptotic stage lose their membrane integrity and additionally incorporate PI. Viable cells are negative for both, annexin V-FITC and PI. The optical density of the controls was equaled to 100%. As can be seen in FIGS. 7 and 8, Dioncoquinone A (1a) and Dioncoquinone B (1b) significantly reduced cell proliferation in tumor cell lines of aggressive B cell lymphoma (DOHH-2, SU-DHL-4) as well as of multiple myeloma (INA-6, RPMI8226), whereas 1a and 1b were non-toxic against normal peripheral mononuclear blood cells (FIG. 9). In case of the human tumor cell line DOHH-1-2 (aggressive B cell lymphoma) the $EC_{50}$ concentration was calculated to be 37 µM for Dioncoquinone A (1a) and 9.4 µM for Dioncoquinone B (1b). For the human tumor cell line SU-DH-4 L (aggressive B cell lymphoma) the $EC_{50}$ was 32 µM for Dioncoquinone A (1a) and 7.6 µM for Dioncoquinone B (1b), for the human tumor cell line INA-6 (multiple myeloma) the $EC_{50}$ was 29 µM for Dioncoquinone A (1a) and 11 µM for Dioncoquinone B (1b), and for the human tumor cell line RPMI8226 (multiple myeloma) the $EC_{50}$ was 58 µM for Dioncoquinone A (1a) and 18 µM for Dioncoquinone B (1b). In experiments using primary mononuclear blood cells (non-malignant cells from peripheral human blood) neither for Dioncoquinone A (1a) or for Dioncoquinone B (1b) a 50% response was achieved within the preferred therapeutic concentration range (FIG. 9).

EXAMPLE 4

Alternative Pathway for the Chemical Synthesis of 1,4-naphthoquinones Having the General Formula 1

A) General Synthesis Pathway

Figure 10:
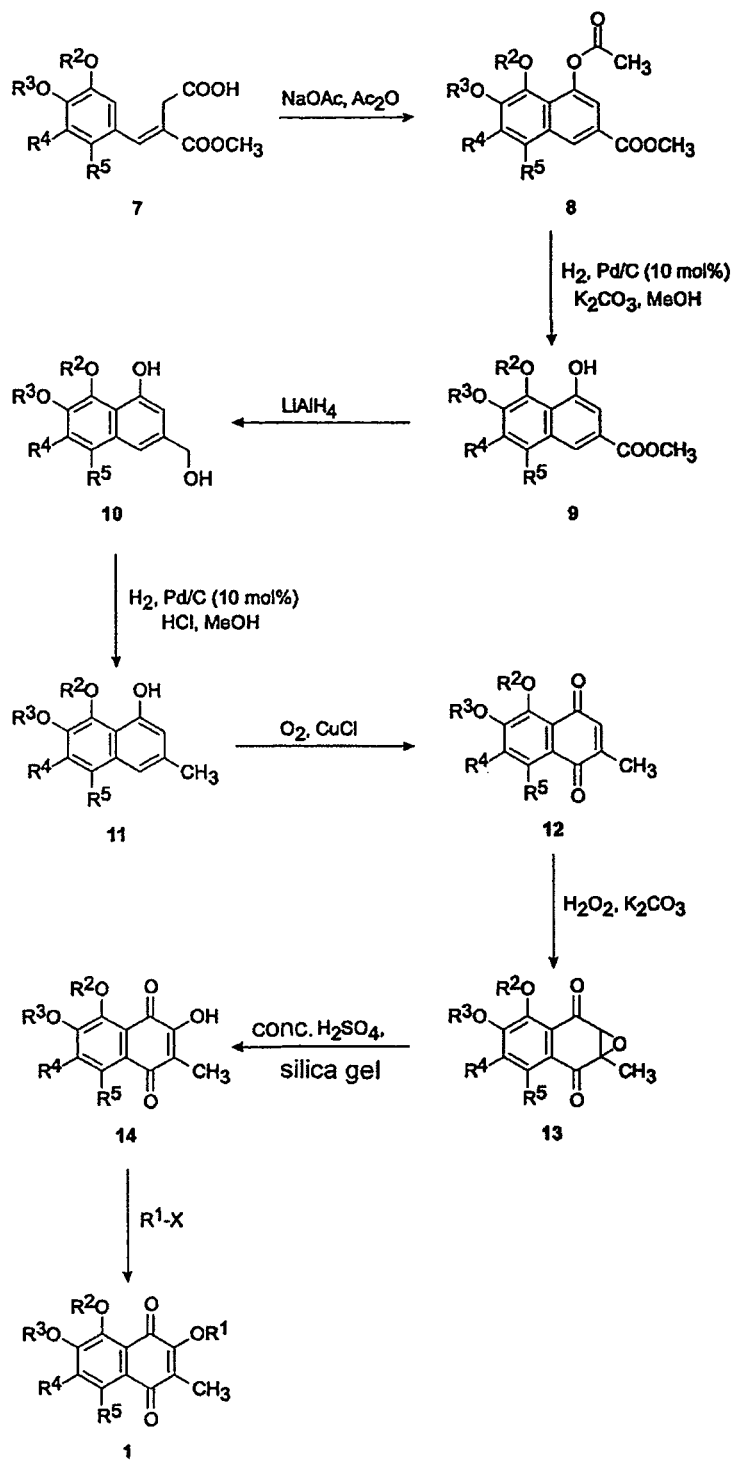
FIG. 10 shows an alternative pathway for the chemical synthesis of 1,4-naphthoquinones having the general formula 1; and Panels A to H of FIG. 11 show the single steps of the chemical synthesis of Dioncoquinone B (1b).

An alternative general pathway for the chemical synthesis of 1,4-naphthoquinones having the general formula 1 is shown in FIG. 10. Starting with arylbutenoic acids having the general formula 7, the naphthalene 8 can be prepared e.g. by treatment with acetic acid anhydride and sodium acetate (analogous to: M. F. Comber, M. V. Sargent, *J. Chem. Soc. Perkin Trans. I*, 1991, 2783-2787). Under basic conditions the naphthalene 8 is converted into the naphthalene derivative 9 (analogous to: D. L. Boger, P. Turnbull, *J. Org. Chem.* 1998, 63, 8004-8011). After complete reduction of the ester group via naphthalene 10 (e.g. by using $LiAlH_4$, followed by $H_2$ under acidic conditions, analogous to: T. D. Nguyen, K. C. F. Leung, M. Liong, C. D. Pentecost, J. F. Stoddart, J. I. Jeffrey, *Org. Lett.* 2006, 8, 3363-3366 and M. A. Rizzacasa, M. V. Sargent, *Aust. J. Chem;* 1988, 41, 1087-1097), the resulting naphthalene 11 is oxidized to the naphthoquinone 12 (using $O_2$ and CuCl, analogous to: L. F. Tietze, C. Giintner, K. M. Gericke, J. Schuberth, G. Bunkoczi, *Eur. J. Org. Chem.* 2005, 70, 2459-2467). The introduction of the hydroxy function at C-3 is achieved by a two-step epoxidation of the electron-deficient double bond of C-2/C-3, followed by opening of the epoxide 13 resulting in the additionally hydroxylated naphthoquinones of the general formula 14 (analogous to: D. A. Henderson, P. N. Collier, G. Pave, P. Rzepa, A. J. P. White, J. N. Burrows, A. G. M. Barret, *J. Org. Chem.* 2006, 71, 2434-2444 and R. Zhu, L. Xing, X. Wang, C. Cheng, B. Liu, Y. Hu, *Synlett* 2007, 14, 2267-2271). The (optional) introduction of group $R^1$ at the hydroxy function of C-3 completes the synthesis of the compounds according to the present invention having the general formula 1.

Figure 11:
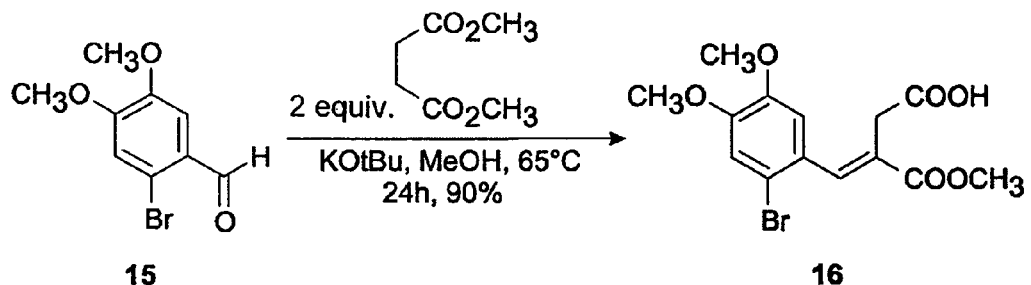
Figure 11:
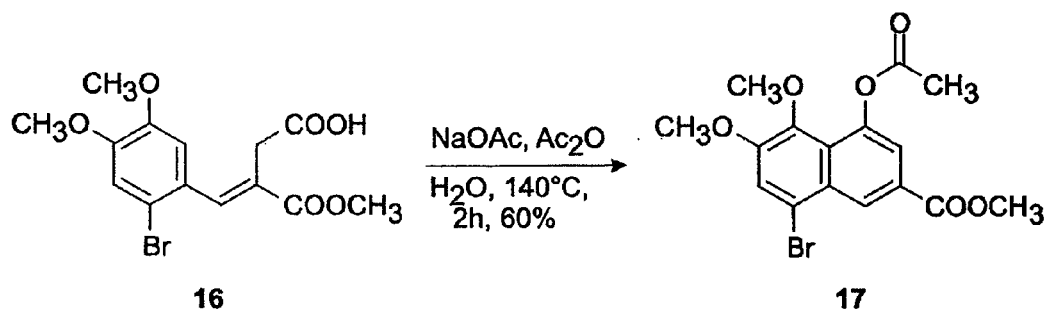
Figure 11:
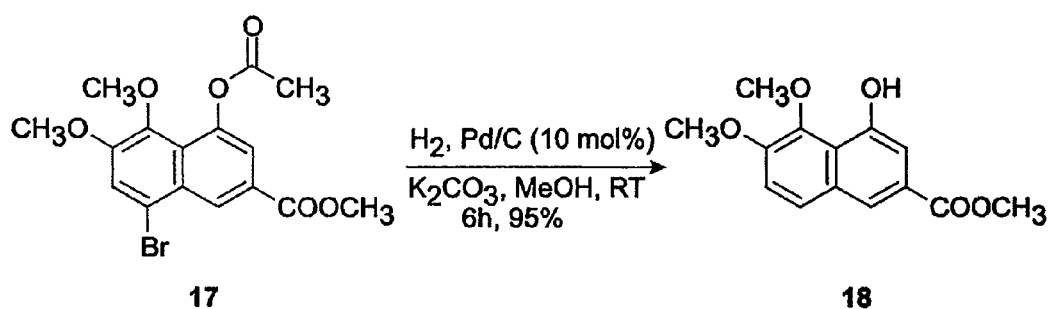
Figure 11:
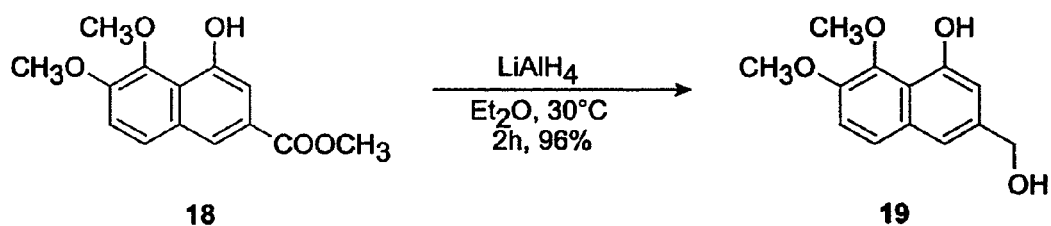
Figure 11:
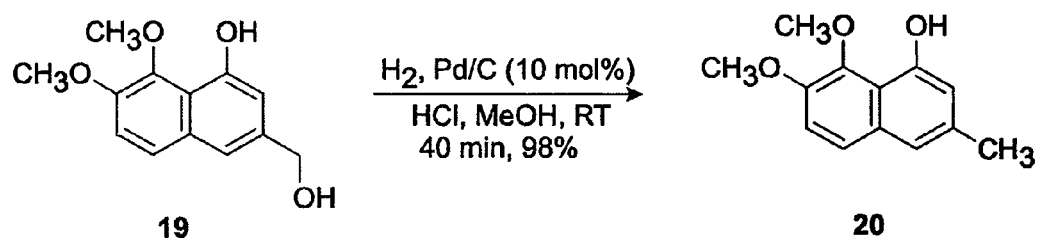
Figure 11:
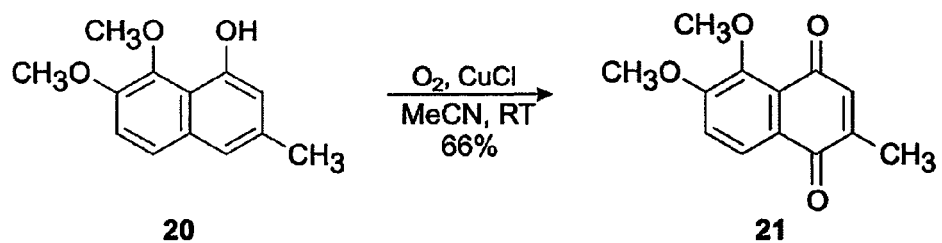
Figure 11:
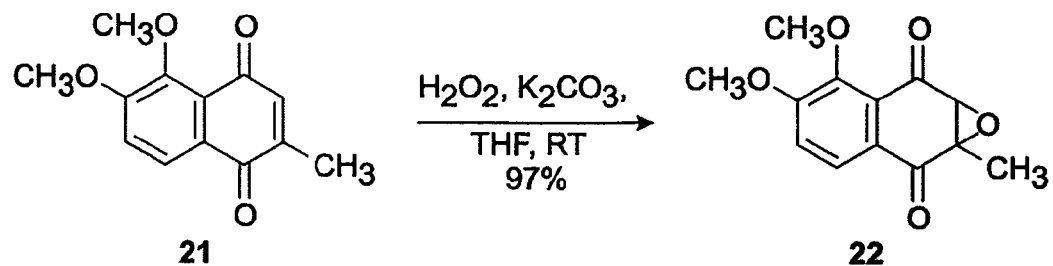
Figure 11:
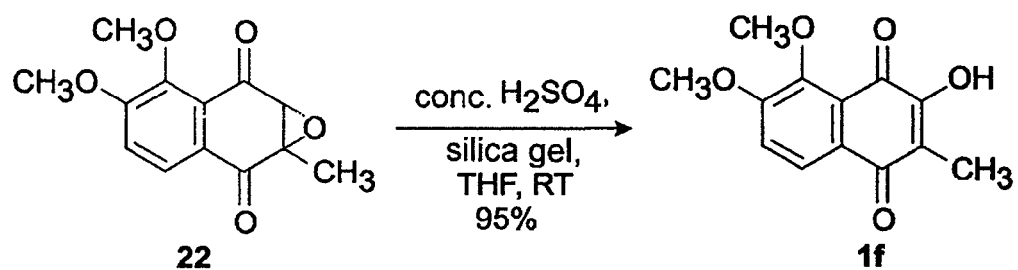
Figure 11:
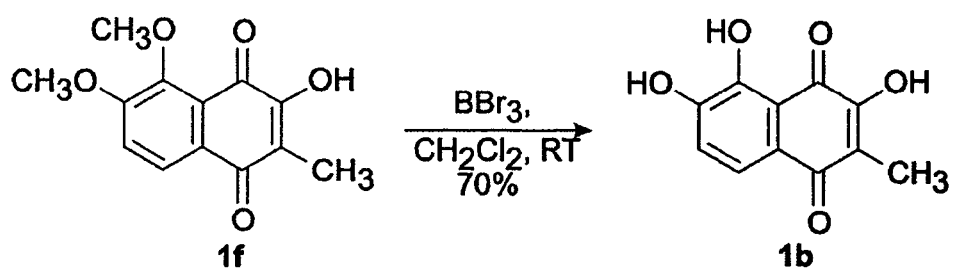

B) Chemical Synthesis of Dioncoquinone B (1b; see FIG. 11)
Preparation of Alkene 16 (FIG. 11A)

775 mg (5.30 mmol, 0.7 ml) dimethylsuccinate and 500 mg (2.04 mmol) 2-bromo-4,5-dimethoxybenzaldehyde (15) were consecutively added to a suspension of 916 mg (8.16 mmol) potassium tert-butanolate in 8 ml absolute methanol under strong stirring (S. Chandrasekhar, N. Ramakrishna Reddy, Y. Srinivasa Rao, *Tetrahedron* 2006, 62, 12098-12107). The mixture was stirred for 48 hours at 80° C. Subsequently, the pH value of the reaction mixture was adjusted to 1-3 using hydrochloric acid (10% aqueous solution), and the solution was extracted with ethyl acetate (3×80 ml). The combined organic phases were washed with 100 ml water and extracted with a 0.5 N solution of sodium hydroxide (3×50 ml). The combined basic aqueous phases were acidified using hydrochloric acid (6 M aqueous solution) and extracted with ethyl acetate (3×100 ml). The combined organic phases were then consecutively washed with 100 ml water and 100 ml saturated sodium chloride solution and dried over sodium sulfate. After removal of the solvent the resulting solid substance was recrystallized in ethyl acetate, and propenoic acid 16 was obtained as a yellow solid substance.

E-3-Methoxycarbonyl-4-(2-bromo-4,5-dimethoxyphenyl)-3-butenoic acid (16)

Yield: 660 mg (1.84 mmol, 90%);
M.p.: 148-150° C.;
IR (ATR insert): $\tilde{v}$=2961 (br w), 2836 (w), 2361 (w), 2111 (w), 1717 (m), 1697 (s), 1596 (m), 1502 (s), 1466 (w), 1436 (m), 1387 (m), 1330 (w), 1262 (s), 1206 (s), 1167 (s), 1092 (s), 1023 (m), 920 (m), 871 (m), 814 (m), 770 (m), 745 (m), 607 (m) cm$^{-1}$;
$^1$H-NMR (CDCl$_3$, 400 MHz): δ=3.52 (s, 2H, CH$_2$), 3.82 (s, 3H, OCH$_3$), 3.84 (s, 3H, OCH$_3$), 3.93 (s, 3H, OCH$_3$), 7.15 (s, 1H, CH), 7.27 (s, 1H, Ar—H), 7.85 (s, 1H, Ar—H), 10.72 (br s, 1H, COOH) ppm;
$^{13}$C-NMR (CDCl$_3$, 100 MHz): δ=δ=34.5, 53.1, 56.5, 56.5, 113.1, 115.5, 115.8, 124.9, 126.8, 142.9, 148.7, 150.6, 168.9, 173.3 ppm;
MS (EI=70 eV): m/z (%)=358 (3) [M–H]$^+$, 279 (100) [M-Br]$^+$, 220 (11) [M-Br—CH$_2$CO$_2$H]$^+$.

Preparation of Naphthalene 17 (FIG. 11B)

2.67 g (7.43 mmol) E-3-methoxycarbonyl-4-(2-bromo-4,5-dimethoxyphenyl)-3-butenoic acid (16) and 612 mg (7.46 mmol) sodium acetate were solved in 300 ml acetic acid anhydride. The batch was stirred for 2 hours at 140° C. and mixed with 1300 ml ice water after cooling to room temperature. Subsequently, the mixture was stirred for 2 hours at room temperature. The precipitated solid was filtered, solved in 100 ml ethyl acetate, and the solution was then washed with a saturated solution of sodium hydrogen carbonate (2×100 ml) in order to remove the educt. Subsequently, the organic phase was dried over sodium sulfate, and the solvent was evaporated by fine vacuum. Naphthalene 17 was obtained as a solid substance with light beige color.

4-Acetoxy-8-bromo-5,6-methoxy-2-naphthoic acid methyl ester (17)

Yield: 1.70 g (4.44 mmol, 60%);
M.p.: 110-113° C.;
IR (ATR insert): $\tilde{v}$=3097 (w), 2956 (w), 2849 (w), 2117 (w), 1767 (m), 1715 (s), 1593 (m), 1467 (m), 1439 (m), 1335 (m), 1281 (m), 1255 (s), 1227 (m), 1195 (s), 1100 (m), 1046 (s), 972 (m), 821 (m), 765 (s), 729 (m), 607 (w) cm$^{-1}$;
$^1$H-NMR (aceton-d$_6$, 400 MHz): δ=2.38 (s, 3H, CH$_3$), 3.90 (s, 3H, OCH$_3$), 3.97 (s, 3H, OCH$_3$), 4.09 (s, 3H, OCH$_3$), 7.67 (d, $^4$J=1.6 Hz, 1H, Ar—H), 7.97 (s, 1H, Ar—H), 8.78 (d, $^4$J=1.6, 1H, Ar—H) ppm;
$^{13}$C-NMR (aceton-d$_6$, 100 MHz): δ=20.8, 52.9, 57.5, 62.0, 119.9, 120.9, 121.8, 127.5, 128.8, 129.2, 143.3, 147.4, 147.4, 153.1, 166.4, 170.1 ppm;
MS (EI=70 eV): m/z (%)=382 (21) [M]$^+$, 340 (100) [M-COCH$_3$+H]$^+$, 325 (51) [M-COCH$_3$—CH$_3$+H]$^+$, 287 (28) [M-Br—CH$_3$—H]$^+$.

Synthesis of Naphthol 18 (FIG. 11C)

390 mg (2.82 mmol) potassium carbonate and 10 mg (0.05%) Pd/C were added to a solution of 216 mg (0.560 mmol) 4-acetoxy-8-bromo-5,6-methoxy-2-naphthoic acid methyl ester (17) in 20 ml methanol. The reaction mixture was stirred for 6 hours at normal pressure and room temperature under H$_2$ atmosphere. Subsequently, the reaction mixture was filtered over celite, and the solution was mixed with 50 ml water and acidified with hydrochloric acid (6 M aqueous solution). The aqueous solution was extracted with dichloromethane (3×30 ml). The combined organic phases were dried over sodium sulfate, and the solvent was evaporated by fine vacuum. Naphthol 18 was obtained as a solid substance with beige color.

4-Hydroxy-5,6-dimethoxynaphthalene-2-carboxylic acid methyl ester (18)

Yield: 139 mg (530 µmol, 95%);
M.p.: 99-100° C. (CH$_2$Cl$_2$);
IR (ATR insert): $\tilde{v}$=3303 (br w), 2944 (w), 1728 (m), 1612 (m), 1578 (w), 1510 (m), 1487 (m), 1371 (m), 1272 (s), 1215 (s), 1093 (m), 1055 (s), 996 (m), 958 (m), 887 (w), 809 (m), 780 (w), 761 (m), 644 (m), 620 (w), 606 (w) cm$^{-1}$;
$^1$H-NMR (CDCl$_3$, 400 MHz): δ=3.94 (s, 3H, OCH$_3$), 4.01 (s, 3H, OCH$_3$), 4.09 (s, 3H, OCH$_3$), 7.30 (d, $^3$J=9.0, 1H, Ar—H), 7.40 (d, $^4$J=1.6 Hz, 1H, Ar—H), 7.69 (d, $^3$J=9.1, 1H, Ar—H), 8.04 (d, $^4$J=1.4, 1H, Ar—H), 9.63 (s, 1H, OH) ppm;
$^{13}$C-NMR (CDCl$_3$, 100 MHz): δ=52.4, 56.9, 63.3, 109.5, 115.6, 120.6, 122.4, 127.1, 127.2, 130.4, 142.9, 149.3, 153.7, 167.3 ppm;
MS (EI=70 eV): m/z (%)=262 (100) [M]$^+$, 247 (48) [M-CH$_3$]$^+$, 231 (9) [M-OCH$_3$]$^+$, 219 (15) [M-CO$_2$H]$^+$.

Synthesis of Naphthalene 19 (FIG. 11D)

A solution of 139 mg (0.530 mmol) 4-hydroxy-5,6-dimethoxynaphthalene-2-carboxylic acid methyl ester (18) in 30 ml diethyl ether was dropped into a suspension of 61 mg (1.59 mmol) lithium aluminium hydride in 3 ml diethyl ether at room temperature. The reaction mixture was stirred for 4 hours at 30° C. Subsequently, the reaction mixture was hydrolyzed with 20 ml hydrochloric acid (6 M aqueous solution) and extracted with dichloromethane (3×20 ml). The combined organic phases were dried over sodium sulfate, and the solvent was evaporated by fine vacuum. Naphthalene 19 was obtained as a solid substance with light yellow color.

4-Hydroxy-2-hydroxymethyl-5,6-dimethoxynaphthalene (19)

Yield: 119 mg (510 µmol, 96%);
M.p.: 80-83° C.;
IR (ATR insert): $\tilde{v}$=3234 (br w), 2937 (w), 2931 (w), 2362 (w), 1643 (w), 1613 (m), 1578 (w), 1514 (m), 1489 (m), 1367 (s), 1148 (m), 1044 (s), 949 (m), 833 (m), 646 (m) cm$^{-1}$;
$^1$H-NMR (CDCl$_3$, 400 MHz): δ=4.03 (s, 3H, OCH$_3$), 4.13 (s, 3H, OCH$_3$), 4.70 (s, 2H, CH$_2$), 5.66 (s, 1H, OH), 6.82 (d, $^4$J=1.4 Hz, 1H, Ar—H), 7.30 (s, 1H, Ar—H), 7.43 (d, $^3$J=9.0, 1H, Ar—H), 7.64 (d, $^3$J=9.0, 1H. Ar—H), 9.55 (s, 1H, OH) ppm;
$^{13}$C-NMR (CDCl$_3$, 100 MHz): δ=57.1, 62.2, 65.5, 109.4, 115.7, 116.6, 117.8, 125.3, 131.6, 138.5, 143.2, 147.5, 153.9 ppm;
MS (EI=70 eV): m/z (%)=234 (100) [M]$^+$, 219 (54) [M-CH$_3$]$^+$, 191 (10) [M-CH$_3$—CH$_2$O+2H]$^+$.

Synthesis of Naphthol 20 (FIG. 11E)

0.05 ml hydrochloric acid (conc.) and 5 mg (0.05%) Pd/C were added to a solution of 100 mg (0.430 mmol) 4-hydroxy-2-hydroxymethyl-5,6-dimethoxynaphthalene (19) in 8 ml methanol. The reaction mixture was stirred for 40 min at room temperature under H$_2$ atmosphere (1 bar). Subsequently, the suspension was filtered over celite, and the filtrate was mixed with 5 ml water and 3 ml hydrochloric acid (6 M aqueous solution). The mixture was extracted with ethyl acetate (3×10 ml), and the combined organic phases were dried over sodium sulfate. After removal of the solvent by fine vacuum, naphthol 20 was obtained as yellow solid substance.

7,8-Dimethoxy-3-methylnaphthol (20)

Yield: 92.0 mg (420 µmol, 98%);

M.p.: 36-37° C., Lit.: 35-37° C. (M Watanabe, S. Hisamatsu, H. Hotokezaka, S. Furukawa, *Chem. Pharm. Bull.* 1986, 34, 2810-2820);

IR (ATR insert): $\tilde{\nu}$=3341 (br w), 2914 (w), 2359 (m), 2341 (m), 1610 (m), 1575 (w), 1356 (m), 1267 (m), 1045 (s), 976 (m), 947 (m), 843 (m), 802 (m), 784 (m), 684 (m) cm$^{-1}$;

$^1$H-NMR (CDCl$_3$, 400 MHz): δ=2.40 (s, 3H, CH$_3$), 3.97 (s, 3H, OCH$_3$), 4.07 (s, 3H, OCH$_3$), 6.71 (d, $^4$J=1.4 Hz, 1H, Ar—H), 7.05 (br s, 1H, Ar—H), 7.20 (d, $^3$J=9.0 Hz, 1H, Ar—H), 7.47 (d, $^3$J=9.0 Hz, 1H, Ar—H), 9.51 (s, 1H, OH) ppm;

$^{13}$C-NMR (CDCl$_3$, 100 MHz): δ=21.7, 57.3, 62.2, 112.5, 115.7, 116.5, 118.3, 124.6, 131.9, 135.6, 143.3. 146.8, 153.3 ppm;

HRMS (ESI): calculated for C$_{13}$H$_{12}$O$_5$Na 240.07569 [M−H+Na]$^+$;

measured 240.07564 [M−H+Na]$^+$.

The physical and spectroscopic data (IR, NMR, MS) are consistent with previously published data (M Watanabe, S. Hisamatsu, H. Hotokezaka, S. Furukawa, *Chem. Pharm. Bull.* 1986, 34, 2810-2820). In contrast to the synthesis disclosed herein, this synthesis step has previously been performed by using a Diels-Alder reaction, which resulted in low yields (~40%) and additionally required the synthesis of the educts.

Synthesis of Dimethoxynaphthoquinone 21 (FIG. 11F)

Air was bubbled through a solution of 70 mg (320 µmol) 7,8-dimethoxy-3-methylnaphthol (20) and 25 mg (250 µmol) Cu(I) chloride in 12 ml acetonitrile for 2 hours. Subsequently, the mixture was mixed with 10 ml water and extracted with dichloromethane (3×20 ml). The combined organic phases were dried over sodium sulfate, and the solvent was evaporated by fine vacuum. After washing the brown residue by column chromatography (silica gel, n-hexane/ethyl acetate, 4:1) dimethoxynaphthoquinone 21 was obtained as an orange solid substance.

5,6-Dimethoxy-2-methyl-1,4-naphthoquinone (21)

Yield: 49.2 mg (210 µmol, 66%);

M.p.: 182-185 C, Lit.: 184-185° C. (M Watanabe, S. Hisamatsu, H. Hotokezaka, S. Furukawa, *Chem. Pharm. Bull.* 1986, 34, 2810-2820);

IR (ATR insert): $\tilde{\nu}$=2928 (br w), 2360 (m), 2342 (m), 1724 (m), 1650 (m), 1626 (m), 1572 (m), 1482 (m), 1443 (m), 1417 (m), 1358 (m), 1330 (m), 1257 (s), 1124 (m), 1062 (s), 1032 (m), 960 (m), 913 (m), 813 (m), 751 (m), 691 (m) cm$^{-1}$;

$^1$H-NMR (CDCl$_3$, 400 MHz): δ=2.14 (d, $^4$J=1.4 Hz, 3H, CH$_3$), 3.92 (s, 3H, OCH$_3$), 3.97 (s, 3H, OCH$_3$), 6.72 (d, $^4$J=1.5 Hz, 1H, Ar—H), 7.18 (d, $^3$J=8.6, 1H, Ar—H), 7.94 (d, $^3$J=8.5 Hz, 1H, Ar—H) ppm;

$^{13}$C-NMR (CDCl$_3$, 100 MHz): δ=16.2, 56.5, 61.5, 115.6, 124.9, 125.7, 126.3, 137.7, 146.7, 149.2, 159.0, 184.6, 184.9 ppm;

MS (EI=70 eV): m/z (%)=232 (100) [M]$^+$, 217 (22) [M-CH$_3$]$^+$;

The physical and spectroscopic data (IR, NMR, MS) are consistent with previously published data (M Watanabe, S. Hisamatsu, H. Hotokezaka, S. Furukawa, *Chem. Pharm. Bull.* 1986, 34, 2810-2820). According to the literature (starting from the corresponding Diels-Alder product) this substance is prepared by oxidation with salcomin obtaining similar yields.

Synthesis of Epoxide 22 (FIG. 11G)

A 1 N solution of potassium carbonate was dropped into a mixture of 35 mg (0.150 mmol) 5,6-dimethoxy-2-methyl-1, 4-naphthoquinone (21) in 4 ml tetrahydrofurane and 1.5 ml hydrogen peroxide solution (30% aqueous solution) at room temperature and under strong stirring until the mixture became colorless. Subsequently, the reaction mixture was mixed with 10 ml of a saturated sodium chloride solution and extracted with ethyl acetate (3×15 ml). The combined organic phases were dried over sodium sulfate, and the solvent was evaporated by fine vacuum. Epoxide 22 was obtained as a solid substance with a light yellow color.

5,6-Dimethoxy-2,3-epoxy-2-methyl-1,4-naphthoquinone (22)

Yield: 36.0 mg (145 µmol, 97%);

M.p.: 151-153° C.;

IR (ATR insert): $\tilde{\nu}$=2925 (w), 2900 (w), 1706 (m), 1687 (s), 1581 (m), 1488 (m), 1451 (m), 1423 (m), 1343 (s), 1277 (s), 1235 (m), 1212 (m), 1171 (w), 1147 (w), 1093 (w), 1060 (m), 1045 (m), 1023 (s), 984 (w), 967 (s), 869 (m), 845 (s), 809 (w), 725 (s), 674 (m), 623 (s) cm$^{-1}$;

$^1$H-NMR (CDCl$_3$, 400 MHz): δ=3.81 (s, 1H, CH), 3.93 (s, 3H, OCH$_3$), 3.95 (s, 3H, OCH$_3$), 7.18 (d, $^3$J=8.6 Hz, 1H, Ar—H), 7.78 (d, $^3$J=8.6 Hz, 1H, Ar—H) ppm;

$^{13}$C-NMR (CDCl$_3$, 100 MHz): δ=14.9, 56.5, 61.9, 62.1, 62.2, 116.3, 124.9, 125.7, 126.7, 148.5, 158.9, 191.7, 191.8 ppm;

HRMS (ESI): calculated for C$_{13}$H$_{12}$O$_5$Na 271.05769 [M+Na]$^+$;

measured 271.05769 [M+Na]$^+$.

Synthesis of Naphthoquinone 1f (FIG. 11H)

20 mg (81 µmol) 5,6-dimethoxy-2,3-epoxy-2-methyl-1,4-naphthoquinone (22) were dissolved in 0.2 ml THF. 116 mg silica gel and 0.1 ml sulphuric acid (conc.) were added to the solution under stirring at room temperature. The solvent was removed at 70° C. and 200 mbar, and the reaction mixture was stirred for another 20 min under the same conditions. The brownish residue was dissolved in 10 ml dichloromethane and washed with 10 ml water. The organic phase was extracted with 5% solution of K$_2$CO$_3$ (3×10 ml) until the dichloromethane phase was colorless. The bright red aqueous phase was adjusted to pH 3 with hydrochloric acid (6 M aqueous solution) and re-extracted with dichloromethane (3×10 ml). The resulting organic phase was dried over sodium sulfate and evaporated. Naphthoquinone 1f was obtained as an orange solid substance.

3-Hydroxy-5,6-dimethoxy-2-methyl-1,4-naphthoquinone (Ancistroquinone C) (1f)

Yield: 19.0 mg (760 µmol, 95%);

M.p.: 218° C. (CH$_2$Cl$_2$), Lit. (isolated natural compound): 217° C. (H$_2$O/MeCN) (S. Rüdenauer, Dissertation, Universität Würzburg, 2008);

IR (ATR): $\tilde{\nu}$=3854 (m), 2923 (w), 2852 (w), 1655 (s), 1637 (m), 1573 (m), 1383 (m), 1359 (m), 1277 (m), 1069 (m), 1026 (w), 740 (w) cm$^{-1}$;

$^1$H-NMR (400 MHz, CDCl$_3$): δ=1.99 (s, 3H, CH$_3$), 3.87 (s, 3H, OCH$_3$), 3.89 (s, 3H, OCH$_3$), 7.11 (d, $^3$J=8.6 Hz, 1H, Ar—H), 7.46 (s, 1H, OH), 7.87 (d, $^3$J=8.6 Hz, 1H, Ar—H) ppm;

MS (EI=70 eV): m/z (%)=248 [M]⁺ (78), 234 [M-CH₂O]⁺ (100), 209 (94), 149 (61).

Synthesis of Dioncoquinone B (1b) (FIG. 11I)

0.12 ml boron tribromide (1 M solution in CH₂Cl₂, 0.120 mmol) were slowly dropped into a solution of 10 mg (40 mol) Ancistroquinone C (10 in 0.2 ml dry dichloromethane at 0° C. The reaction mixture was warmed up to room temperature and stirred for 2 hours. Subsequently, the reaction mixture was mixed with 4 ml water and extracted with dichloromethane (3×10 ml). The combined organic phases were re-extracted with a 5% solution of K₂CO₃ (3×10 ml). The aqueous phase was acidified with hydrochloric acid (6 M aqueous solution) and extracted with dichloromethane (3×20 ml). The combined organic phases were dried over sodium sulfate, and the solvent was evaporated by fine vacuum. The resulting orange solid substance was recrystallized from chloroform, and the natural compound Dioncoquinone B (1b) was obtained as orange-red solid substance.

3,5,6-Trihydroxy-2-methyl-1,4-naphthoquinone (Dioncoquinone B) (1b)

Yield: 7.00 mg (30.0 μmol, 70%);

M.p.: 216-217° C. (CH₂Cl₂), Lit. (isolated natural compound): 218° C. (CDCl₃) (S. Rüdenauer, Dissertation, Universitat Würzburg, 2008; G. Bringmann, S. Rüdenauer, A. Irmer, T. Bruhn, R. Brun, T. Heimberger, T. Stühmer, R. Bargou, M. Chatterjee, *Phytochemistry* 2008, 69, 2501-2509);

IR (ATR insert): $\tilde{v}$=3393 (br m), 2853 (w), 2093 (w), 1621 (s), 1583 (w), 1458 (m), 1389 (w), 1289 (s), 1209 (m), 1103 (m), 1048 (w), 845 (w), 747 (w), 729 (w), 625 (m);

¹H-NMR (CDCl₃, 400 MHz): δ=2.09 (s, 1H, CH₃), 6.08 (br s, 1H, OH), 7.04 (br s, 1H, OH), 7.18 (d, ³J=8.2 Hz, 1H, Ar—H), 7.64 (d, ³J=8.2 Hz, 1H, Ar—H), 11.20 (br s, 1H, OH) ppm;

¹³C-NMR (CDCl₃, 100 MHz,): δ=9.1, 113.3, 120.6, 121.6, 123.0, 124.6, 148.2, 149.9, 152.6, 183.6, 185.3 ppm;

MS (EI=70 eV): m/z (%)=234 (100) [M]⁺, 219 (54) [M-CH₃]⁺, 191 (10) [M-CH₃—CH₂O+2H]⁺.

The physical and spectroscopic data are consistent with those of the isolated natural compound (see Example 1). For additional confirmation of the molecular structure, a co-NMR of the isolated and of the chemically synthesized compound was performed. The co-NMR showed a 100% correlation of the signals (no double peaks).

The invention claimed is:

1. A method of treating multiple myeloma or B-cell lymphoma comprising administering to a patient in need of such treatment a therapeutically effective amount of a compound having the general formula,

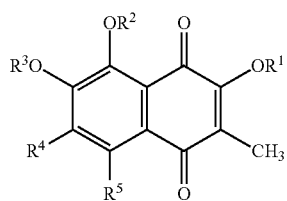

wherein

R¹, R², and R³ are independently selected from the group consisting of (a) H, (b) a C₁-C₁₈ alkyl, wherein said alkyl is straight, branched or cyclic, (c) a C₁-C₁₈ alkenyl, wherein said alkenyl is straight, branched or cyclic, (d) an aryl or heteroaryl, (e) an acyl group or acyl groups being branched, heteroatom-substituted or aryl-substituted, (f) a sugar or another acetal, and (g) a sulfonyl group;

R⁴ and R⁵ are independently selected from the group consisting of (a') H, (b') a C₁-C₁₈ alkyl, wherein said alkyl is straight, branched or cyclic, (c') a C₁-C₁₈ alkenyl, wherein said alkenyl is straight, branched or cyclic, (d') an aryl or heteroaryl, (e') an acyl group or acyl groups being branched, heteroatom-substituted or aryl-substituted, (f') a C- or O-linked sugar or another acetal, (g') —OH or —SH, (h') an alkoxy group, wherein the alkyl group of said alkoxy group is straight, branched or cyclic, (i') an alkyl group bound via a sulfur atom, (j') a sulfonyl group, (k') —NH₂, —NHR, —NRR', —NC or —NO₂, and (l') —Fl, —Cl, —Br, —I, —CN; wherein R and R' are, independently, alkyl, aryl, heteroaryl, alkenyl, alkynyl, acyl, or sulfonyl group; and R³ and R⁴ as well as R⁴ and R⁵ are optionally linked, thereby resulting in a ring;

as well as salts thereof.

2. A method of producing a compound selected from the group consisting of compounds having formula

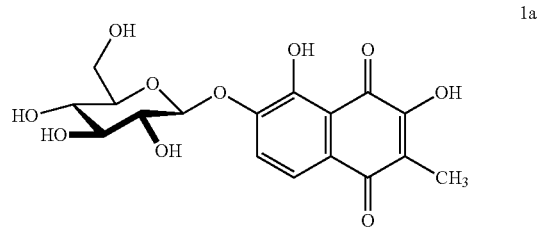

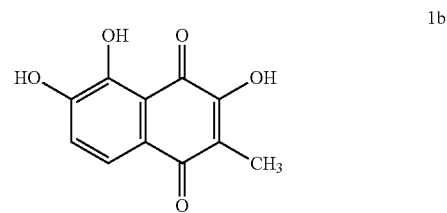 [SMILES: CC1=C(O)C(=O)c2c(ccc(O)c2O)C1=O]

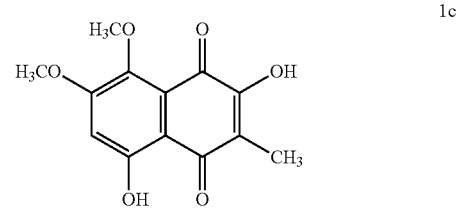 [SMILES: COc1cc(O)c2c(c1OC)C(=O)C(O)=C(C)C2=O]

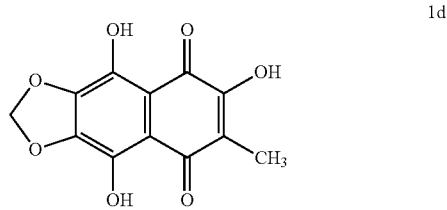 [SMILES: CC1=C(O)C(=O)c2c(O)c3c(c(O)c2C1=O)OCO3]

-continued

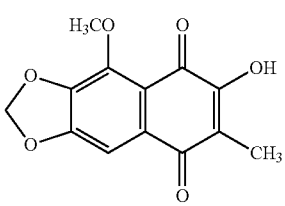
1e and salts thereof, wherein said method comprises the cultivation of callus cultures of a tropical liana of a family selected from Dioncophyllaceae, Ancistrocladaceae, Drosophvllaceae, Droseraceae, Nepenthaceae, Plumbaginaceae, Malyaceae, and Ebenaceae, and isolation of at least one of said compounds.

3. The method according to claim 1, wherein said compound has the general formula

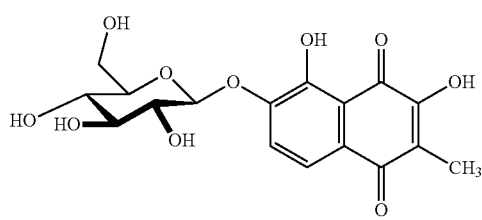
1a as well as diastereomers and enantiomers, and salts thereof.

4. The method according to claim 1, wherein said compound has the general formula

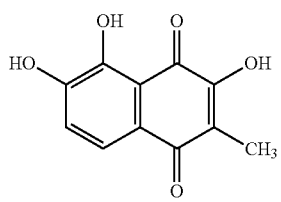
1b as well as salts thereof.

5. The method according to claim 1, wherein said compound has the general formula

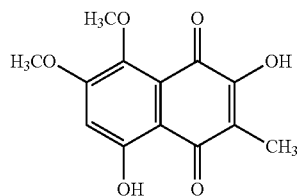
1c as well as salts thereof.

6. The method according to claim 1, wherein said compound has the general formula

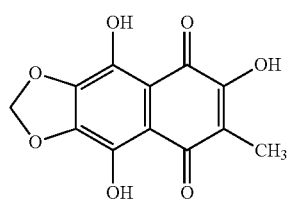
1d as well as salts thereof.

7. The method according to claim 1, wherein said compound has the general formula

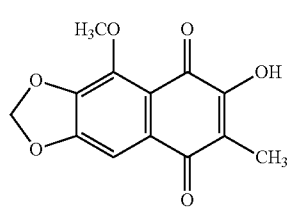
1e as well as salts thereof.

8. The method according to claim 2, wherein said cultivation comprises a step of reducing the main nutrition elements in the culture medium and the concomitant increase of the concentration of divalent ions in comparison to the other main nutrition elements.

9. The method according to claim 1, wherein one or more of said $R^1$, $R^2$, $R^3$, $R^4$, $R^5$, R and R' is a benzyl group.

* * * * *

UNITED STATES PATENT AND TRADEMARK OFFICE
CERTIFICATE OF CORRECTION

PATENT NO.        : 8,877,718 B2
APPLICATION NO.   : 12/865333
DATED             : November 4, 2014
INVENTOR(S)       : Gerhard Bringmann et al.

It is certified that error appears in the above-identified patent and that said Letters Patent is hereby corrected as shown below:

In the Specification

Column 3,
Line 20, "(f) an" should read --(f') an--.

Column 14,
Line 40, "naphthoquione," should read --naphthoquinone--.

Column 14,
Line 52, "methylendioxy-" should read --methylenedioxy--.

Column 18,
Line 36, "Giintner," should read --Güntner,--.

Column 23,
Line 5, "(40 mol)" should read --(40 μmol)--.

Column 23,
Line 6, "C (10 in 0.2" should read --C (1f) in 0.2--.

Column 23,
Lines 29-30, "Universitat" should read --Universität--.

In the Claims

Column 25,
Line 14, Claim 2, "Drosophvllaceae," should read --Drosophyllaceae,--.

Signed and Sealed this
Fourth Day of August, 2015

Michelle K. Lee
*Director of the United States Patent and Trademark Office*